US011215611B2

(12) United States Patent
Matsumura et al.

(10) Patent No.: US 11,215,611 B2
(45) Date of Patent: *Jan. 4, 2022

(54) RESIN-PLATINUM COMPOSITE AND USAGE THEREOF

(71) Applicant: NIPPON STEEL Chemical & Material Co., Ltd., Tokyo (JP)

(72) Inventors: Yasufumi Matsumura, Tokyo (JP); Yasushi Enomoto, Tokyo (JP)

(73) Assignee: NIPPON STEEL Chemical & Material Co., Ltd., Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 15/743,277

(22) PCT Filed: Jul. 7, 2016

(86) PCT No.: PCT/JP2016/070082
§ 371 (c)(1),
(2) Date: Jan. 10, 2018

(87) PCT Pub. No.: WO2017/010391
PCT Pub. Date: Jan. 19, 2017

(65) Prior Publication Data
US 2018/0209965 A1    Jul. 26, 2018

(30) Foreign Application Priority Data
Jul. 11, 2015   (JP) .............. JP2015-139269

(51) Int. Cl.
*G01N 33/532* (2006.01)
*G01N 33/558* (2006.01)
*G01N 33/543* (2006.01)
*G01N 33/553* (2006.01)
*G01N 33/545* (2006.01)
*C08J 3/12* (2006.01)

(52) U.S. Cl.
CPC ............ *G01N 33/532* (2013.01); *C08J 3/128* (2013.01); *G01N 33/543* (2013.01); *G01N 33/545* (2013.01); *G01N 33/54386* (2013.01); *G01N 33/553* (2013.01); *G01N 33/558* (2013.01); *C08J 2339/08* (2013.01)

(58) Field of Classification Search
CPC ..... C08J 2339/08; C08J 3/128; G01N 33/532; G01N 33/543; G01N 33/54386; G01N 33/545; G01N 33/553; G01N 33/558
See application file for complete search history.

(56) References Cited

U.S. PATENT DOCUMENTS

| | | | | |
|---|---|---|---|---|
| 10,690,665 B2* | 6/2020 | Matsumura | ........... | G01N 33/558 |
| 2005/0032244 A1* | 2/2005 | Nie | ........... | B01J 19/0046 506/12 |
| 2005/0208543 A1 | 9/2005 | Vann et al. | | |
| 2010/0136566 A1 | 6/2010 | Mehra et al. | | |
| 2012/0329935 A1* | 12/2012 | Matsumura | ........... | C09D 5/32 524/434 |
| 2015/0064718 A1* | 3/2015 | Caracci | ........... | C08K 3/22 435/7.5 |
| 2017/0168049 A1* | 6/2017 | Matsumura | ........... | G01N 33/553 |
| 2017/0219574 A1* | 8/2017 | Matsumura | ........... | C08K 3/08 |
| 2020/0240987 A1* | 7/2020 | Matsumura | ........... | G01N 33/54346 |

FOREIGN PATENT DOCUMENTS

| | | |
|---|---|---|
| CN | 102460792 | 5/2012 |
| CN | 102782024 | 11/2012 |
| CN | 102822249 | 12/2012 |
| CN | 102947688 | 2/2013 |
| CN | 106661238 | 5/2017 |
| CN | 106662585 | 5/2017 |
| EP | 2579022 | 4/2013 |
| EP | 2674744 | 12/2013 |
| JP | H03206959 | 9/1991 |
| JP | H0510950 | 1/1993 |
| JP | 2956030 | 7/1999 |

(Continued)

OTHER PUBLICATIONS

Kanahara et al., "Fabrication of gold nanoparticle-polymer composite particles with raspberry, core-shell and amorphous morphologies at room temperature via electrostatic interactions and diffusion," Soft Matter, Jan. 14, 2014, vol. 10, issue 2, pp. 275-280; first published on Oct. 11, 2013.*

Hifumi et al., "Immunochemical detection of methamphetamine using polymer-protected ultrafine platinum particles," J. Ferment. Bioeng., 1996, vol. 82, issue 4, pp. 417-419.*

Kensuke Akamatsu et al., Synthesis of pH-Responsive Nanocomposite Microgels with Size-Controlled Gold Nanoparticles from Ion-Doped, Lightly Cross-Linked Poly(vinylpyridine), Langmuir, 2010, vol. 26, No. 2, Oct. 9, 2009,pp. 1254-1259.

(Continued)

Primary Examiner — Galina M. Yakovleva

(74) Attorney, Agent, or Firm — JCIPRNET

(57) ABSTRACT

This resin-platinum composite 100 is provided with resin particles 10 and platinum particles 20, and the platinum particles 20 are immobilized on the resin particles 10. In the resin-platinum composite 100, one portion of the platinum particles 20 may be distributed three-dimensionally on surface layer sections 60 of the resin particles 10. In this case, the one portion of the three-dimensionally distributed platinum particles 20 may be partially exposed outside the resin particles 10, and the remaining portion may be enclosed in the resin particles 10. In the platinum particles 20, enclosed particles 30 that are fully enclosed in the resin particles 10, partially exposed particles 40 each having a segment embedded inside the resin particles 10 and a segment exposed outside the resin particles 10, and surface attached particles 50 attached to the surfaces of the resin particles 10 preferably exist.

11 Claims, 4 Drawing Sheets

(56) References Cited

FOREIGN PATENT DOCUMENTS

| JP | 2003262638 | 9/2003 |
|---|---|---|
| JP | 2007521460 | 8/2007 |
| JP | 2009168495 | 7/2009 |
| JP | 2009192270 | 8/2009 |
| JP | 2011117906 | 6/2011 |
| JP | 2012242162 | 12/2012 |
| JP | 2013522653 | 6/2013 |
| JP | 2015068764 | 4/2015 |
| TW | 200925199 | 6/2009 |
| TW | 201210799 | 3/2012 |
| WO | 2011108250 | 9/2011 |
| WO | 2011148870 | 12/2011 |

OTHER PUBLICATIONS

"International Search Report (Form PCT/ISA/210) of PCT/JP2016/070082", dated Sep. 27, 2016, with English translation thereof, pp. 1-4.

V.G.Pol et al., "Coating Noble Metal Nanocrystals (Ag, Au, Pd, and Pt) on Polystyrene Spheres via Ultrasound Irradiation," Langmuir, vol. 21, No. 8, Apr. 12, 2005, pp. 3635-3640.

Feng Chiao, "Preparation of platinum nanoparticles/ polymer composite microsphere and their catalytic properties", Jiangnan University, Jul. 2009,with English abstract, pp. 1-50.

Alexandre Dokoutchaev et al., "Colloidal Metal Deposition onto Functionalized Polystyrene Microspheres," Chem. Mater., vol. 11, No. 9, Aug. 17, 1999, pp. 2389-2399.

Jung-Hyun Lee et al."Facile Preparation of Highly-Scattering Metal Nanoparticle-Coated Polymer Microbeads and Their Surface Plasmon Resonance," vol. 131, J. Am. Chem. Soc. Mar. 24, 2009, pp. 5048-5049.

"Office Action of China Counterpart Application," dated Mar. 29, 2019, with English translation thereof, p. 1-p. 19.

"Search Report of Europe Counterpart Application", dated Nov. 14, 2018, p. 1-p. 11.

Prince Manta, et al., "Formulation, Development and Sensitivity, Specificity Comparison of Gold, Platinum and Silver Nano Particle Based HIV ½ and HCG IVD Rapid Test Kit (Immune Chromatoghraphic Test Device)," World Journal of Pharmacy and Pharmaceutical Sciences, vol. 4, Apr. 2015, pp. 1870-1905.

Chen Yi-Yong, et al., "Synthesis and properties of 1-(2-aminoethyl)piperazine resin used in the sorption of the platinum group and gold ions," Reactive Polymers, vol. 23, May 1994, pp. 165-172.

"Office Action of Japan Counterpart Application," dated Mar. 31, 2020, with English translation thereof, p. 1-p. 9.

"Office Action of Taiwan Counterpart Application," with machine English translation thereof, dated Dec. 4, 2019, p. 1-p. 11.

Office Action of Taiwan Counterpart Application, with English translation thereof, dated May 11, 2020, pp. 1-14.

"Office Action of Taiwan Counterpart Application," with English translation thereof, dated Jun. 25, 2019, p. 1-p. 9.

"Office Action of Korea Counterpart Application," with English translation thereof, dated Jul. 20, 2019, p. 1-p. 7.

Office Action of China Counterpart Application, with English translation thereof, dated Mar. 18, 2020, pp. 1-26.

Ryo Tanaka et al., "A novel enhancement assay for immunochromatographic test strips using gold nanoparticles.", Analytical and Bioanalytical Chemistry, vol. 385, Issue 8, Jul. 13, 2006, pp. 1414-1420.

Jong Min Park et al., "Chemiluminescence lateral flow immunoassay based on Pt nanoparticle with peroxidase aclivily", Analytica Chimica Acta, vol. 853, Issue 1, Jan. 1, 2015, pp. 360-367.

"Office Action of Korea Counterpart Application", dated Sep. 25, 2020, with English translation thereof, pp. 1-7.

"Office Action of China Counterpart Application", dated Sep. 27, 2020, with English translation thereof, pp. 1-26.

"Search Report of Europe Counterpart Application", dated Jul. 8, 2021, p. 1-p. 12.

"Office Action of Korea Counterpart Application" with English translation thereof, dated Sep. 27, 2021, p. 1-p. 8.

\* cited by examiner

RESIN-PLATINUM COMPOSITE AND USAGE THEREOF

CROSS-REFERENCE TO RELATED APPLICATION

This application is a 371 application of the international PCT application serial no. PCT/JP2016/070082, filed on Jul. 7, 2016, which claims the priority benefit of Japan application no. 2015-139269, filed on Jul. 11, 2015. The entirety of each of the above-mentioned patent applications is hereby incorporated by reference herein and made a part of this specification.

TECHNICAL FIELD

The present invention relates to, for example, a resin-platinum composite that can be preferably used for applications such as immunological measurement, a labeling substance using the same, an immunological measurement method, a reagent for immunological measurement, an analyte measurement method, an analyte measurement kit, and a test strip for lateral flow chromatography.

BACKGROUND ART

Since there are numerous chemical substances in a living body, a technique for quantitatively and quantitatively analyzing a specific trace component in a living body is very important. In the fields of medicine, pharmaceuticals, health foods, biotechnology, environment, and the like, chemicals and foods that act only in specific parts (chemical substances) in a living body, analyzing devices and diagnostic agents for detecting small changes in a living body, and the like have been developed together with such techniques.

An immunoassay is one of the above analysis techniques. This is also called an immunological measurement method, and is a method of quantitatively and quantitatively analyzing a trace component using a specific reaction between an antigen and an antibody which is one of immunologic reactions. A reaction between an antigen and an antibody is widely used in the above fields because sensitivity and reaction selectivity are high. There are various measurement methods according to measurement principles of the immunoassay. For example, an enzyme immunoassay (EIA), a radioimmunoassay (RIA), a chemiluminescence immunoassay (CLIA), a fluorescence immunoassay (FIA), a latex agglutination method (LIA, PA), immunochromatography (ICA), a hemagglutination method (HA), a hemagglutination inhibition method (HI), and the like are exemplified. In addition, a physical and chemical measurement method, a biological measurement method, and the like are exemplified in addition to the immunoassay.

In the immunoassay, antigens or antibodies are qualitatively or quantitatively detected from a change (change in concentration of antigens, antibodies or composites) when antigens and antibodies react to form composites. When these are detected, if a labeling substance binds to antibodies, antigens or composites, detection sensitivity increases. Therefore, a labeling ability of the labeling substance is an important factor that affects a detection ability in the immunoassay. In the immunoassays exemplified above, an erythrocyte (in the case of HA), a latex particle (in the case of LIA), a fluorescent dye (in the case of FIA), a radioactive element (in the case of RIA), an enzyme (in the case of EIA), a chemiluminescent substance (in the case of CLIA), and the like are used as the labeling substance.

Incidentally, when colored fine particles are used as a labeling substance, since it is possible to visually confirm that a change is detected without using a special analyzing device, more convenient measurement is expected. Examples of such colored fine particles include colloidal particles of metals and metal oxides, and latex particles colored with a dye (for example, Patent Literature 1 and Patent Literature 4). However, since a color tone of the colloidal particles is determined according to the particle size and preparation conditions, there is a problem in that it is difficult to obtain a desired vivid and dark color tone, that is, visibility is insufficient.

In addition, the colored latex particles have a problem in that an effect of coloring with a dye is weak, and visual determination is insufficient. Here, when a coloring amount of a dye is increased in order to address this problem, since the dye covers the surface of the latex and an original state of the surface of the latex particles is impaired, there is a problem in that it is difficult to bind antigens or antibodies. In addition, there is a problem in that clogging of pores of a chromatographic medium such as a membrane filter, nonspecific aggregation of latex particles, and dark coloring due to an increase in a coloring material of a dye do not necessarily result in improvement in performance.

An immunochromatographic method in which, in order to improve visibility of the above labeling substance, an antibody (labeled antibody) to which the labeling substance is bound reacts with an antigen to form a composite, another metal is then additionally modified with respect to these labeling substance, and thus detection sensitivity of the labeling substance is amplified has been disclosed (Patent Literature 2 and 5). However, in this method, the operation is complicated and stable amplification is difficult. In addition, measurement cost is high because a special device is necessary, and thus applicable applications and usage environments can be considered to be limited.

In addition, colored latex including gold nanoparticles bound to the surface of polymer latex particles has been disclosed (Patent Literature 3).

When gold nanoparticles are bound to the surface of the polymer latex particles, the gold nanoparticles themselves are a colorant and contribute to improvement in visual determination and detection sensitivity, and the gold nanoparticles themselves have an excellent ability to bind to an antigen or an antibody. Therefore, even if the gold nanoparticles are bound to an extent at which a sufficient dark color is obtained, a sufficient amount of antigen or antibody can be bound.

The colored latex is obtained by binding gold nanoparticles to the surface of the latex by emitting gamma rays to a dispersion of a styrene-acrylic acid copolymer latex and HAuCl which is a precursor of gold nanoparticles. However, in the colored latex, since gold nanoparticles are bound to only the surface of the latex, there is a limitation on a supported amount of gold particles at which surface plasmon resonance is exhibited, and the gold nanoparticles are likely to be detached. As a result, there is a risk of visibility and sensitivity as a reagent for immunological measurement not being sufficient. In addition, since electromagnetic radiation such as gamma rays is emitted, there is a risk of the latex being damaged. Furthermore, in the specification in Patent Literature 3, preferable ranges of the diameter of the latex and the size of the gold nanoparticles are disclosed. However, in examples, it is not clear whether verification is performed in such preferable ranges and there is no basis for defining the preferable ranges.

In addition, in Patent Literature 4, polymer latex particles covered with a metal (gold) are disclosed, and an application to a reagent that can be used for a microscopic examination and an immunoassay method is suggested.

However, in the polymer latex particles covered with the metal (gold), the material and the particle size of the polymer latex particles are not disclosed. In addition, there is no verification regarding an effect as a reagent that can be used for an immunoassay method. Therefore, the effect as a reagent in the metal (gold) and polymer latex particles is unknown.

In addition, in Non-Patent Literature 1, a microgel in which gold nanoparticles are supported on poly-2-vinylpyridine latex particles is disclosed. The pH responsiveness of the particle size of the microgel is confirmed from a change in movement of localized surface plasmon resonance of the gold nanoparticles. However, in the microgel, the gold nanoparticles are supported on a single layer near the surface layer of the latex particles. Therefore, a supported amount of the gold nanoparticles is small and a dark color tone effective for the immunoassay cannot be considered to be obtained. In addition, the material, the structure, and the composition of the microgel and the like have not been studied, and an effect on a specific application such as an immunological measurement reagent is unknown.

As described above, latex particles with gold nanoparticles bound thereto or covered therewith are expected as a reagent for immunological measurement. However, in the techniques of the related art, the durability and visibility are not sufficient. In addition, even if they have high visibility, applicable applications and usage environments are limited.

REFERENCE LIST

Patent Literature

Patent Literature 1: Japanese Patent Application Laid-Open No. H5-10950
Patent Literature 2: Japanese Patent Application Laid-Open No. 2011-117906
Patent Literature 3: Japanese Patent Application Laid-Open No. 2009-168495
Patent Literature 4: Japanese Patent Application Laid-Open No. H3-206959
Patent Literature 5: Japanese Patent Application Laid-Open No. 2009-192270

Non-Patent Literature

Non-Patent Literature 1: K. Akamatsu, M. Shimada, T. Tsuruoka, H. Nawafune, S. Fujii and Y. Nakamura; Langmuir 2010, 26, 1254-1259.

SUMMARY

Technical Problem

In order to use a resin-metal composite as a labeling substance in immunological measurement, it is necessary to stably bind it to a ligand such as an antibody. However, when the ligand is labeled with a resin-metal composite, even if a stable binding state is obtained, excellent detection sensitivity is not necessarily obtained. For example, fine resin-metal composites are likely to aggregate. When aggregation occurs, not only a handling property significantly deteriorates, but also a deviation occurs in the concentration of the resin-metal composite which is a labeling substance and detection sensitivity significantly deteriorates.

An object of the present invention is to provide a resin-metal composite that is less likely to aggregate while it is bound to a ligand such as an antibody and has an excellent handling property, and, for example, in immunological measurement, to provide a resin-metal composite for immunological measurement in which determination with high sensitivity is possible.

Solution to Problem

The inventors have conducted extensive studies and as result, found that the above problems can be addressed using a resin-platinum composite in which a plurality of platinum particles are fixed to a resin particle, and completed the present invention.

That is, the resin-platinum composite of the present invention includes a resin particle, and a plurality of platinum particles that are relatively smaller than the resin particle, wherein the plurality of platinum particles are fixed to the resin particle.

In the resin-platinum composite of the present invention, at least some of the platinum particles may be distributed three-dimensionally on a surface layer section of the resin particle. In this case, 60 wt % to 100 wt % of the plurality of platinum particles may be in the surface layer section.

In the resin-platinum composite of the present invention, the platinum particles may be fixed to the surface of the resin particle without being superimposed in a radial direction of the resin particle.

In the resin-platinum composite of the present invention, an average particle size of the platinum particles is in a range of 1 to 80 nm. In this case, the average particle size of the resin-platinum composite may be in a range of 50 to 1000 nm.

In the resin-platinum composite of the present invention, an average particle size of the platinum particles is preferably in a range of 1 to 50 nm, more preferably in a range of 1 to 30 nm, and most preferably in a range of 1 to 15 nm. In this case, the average particle size of the resin-platinum composite is preferably in a range of 100 to 600 nm.

In the resin-platinum composite of the present invention, a supported amount of the platinum particles may be in a range of 5 wt % to 70 wt % with respect to a weight of the resin-platinum composite.

In the resin-platinum composite of the present invention, the resin particle may be a polymer particle having a structure including a substituent to which platinum ions are able to be attached.

A labeling substance of the present invention includes any one of the resin-platinum composites described above. In this case, the labeling substance may be used by attaching an antigen or an antibody to the surface of the resin-platinum composite.

In an immunological measurement method of the present invention, any one of the labeling substances described above is used.

A reagent for immunological measurement of the present invention includes any one of the resin-platinum composites described above.

An analyte measurement method of the present invention is a method of detecting or quantifying an analyte contained in a sample. The analyte measurement method includes performing the following Processes (I) to (III) using a test strip for lateral flow chromatography that includes a membrane and a determination section to which a capture ligand that specifically binds to the analyte is fixed in the membrane:

Process (I): a process of contacting the analyte contained in the sample with a labeled antibody obtained by labeling an antibody that specifically binds to the analyte with any one of the resin-platinum composites described above;

Process (II): a process of contacting a composite including the analyte and the labeled antibody formed in Process (I) with the capture ligand in the determination section; and Process (III): a process of measuring a color development intensity derived from localized surface plasmon resonance and light energy absorption due to electron transition of the resin-platinum composite.

An analyte measurement kit of the present invention is an analyte measurement kit for detecting or quantifying an analyte contained in a sample using a test strip for lateral flow chromatography. The analyte measurement kit includes a test strip for lateral flow chromatography that includes a membrane and a determination section to which a capture ligand that specifically binds to the analyte is fixed in the membrane; and a detection reagent including a labeled antibody obtained by labeling an antibody that specifically binds to the analyte with any one of the resin-platinum composites described above.

A test strip for lateral flow chromatography of the present invention detects or quantifies an analyte contained in a sample. The test strip for lateral flow chromatography includes a membrane; a determination section to which a capture ligand that specifically binds to the analyte is fixed in a direction in which the sample is developed in the membrane; and a reaction section that is upstream from the determination section and includes a labeled antibody obtained by labeling an antibody that specifically binds to the analyte with any one of the resin-platinum composites described above.

Advantageous Effects of Invention

The resin-platinum composite of the present invention has excellent dispersibility, for example, while it is bound to a ligand such as an antibody and is less likely to aggregate. In addition, since the resin-platinum composite of the present invention has a structure in which a plurality of platinum particles are fixed to a resin particle, a supported amount of platinum particles is large, and the platinum particles are less likely to be detached from the resin particle. In addition, the platinum particles also exhibit light energy absorption due to electron transition in addition to localized surface plasmon resonance. Therefore, the resin-platinum composite of the present invention is a material excellent in a handling property, durability, visibility, visual determination, and detection sensitivity, and can be preferably applied for the purpose of labeling substances for immunological measurement, for example, EIA, RIA, CLIA, FIA, LIA, PA, ICA, HA, and HI, reagents for immunological measurement, drugs, solid catalysts, pigments, paints, conductive materials, electrodes, sensor elements, and the like. When the resin-platinum composite of the present invention is used for immunological measurement, it is possible to obtain an excellent handling property, durability and visibility and it is possible to perform determination with high sensitivity without addition of a special device or operation process.

DESCRIPTION OF THE EMBODIMENTS

Figure 1:
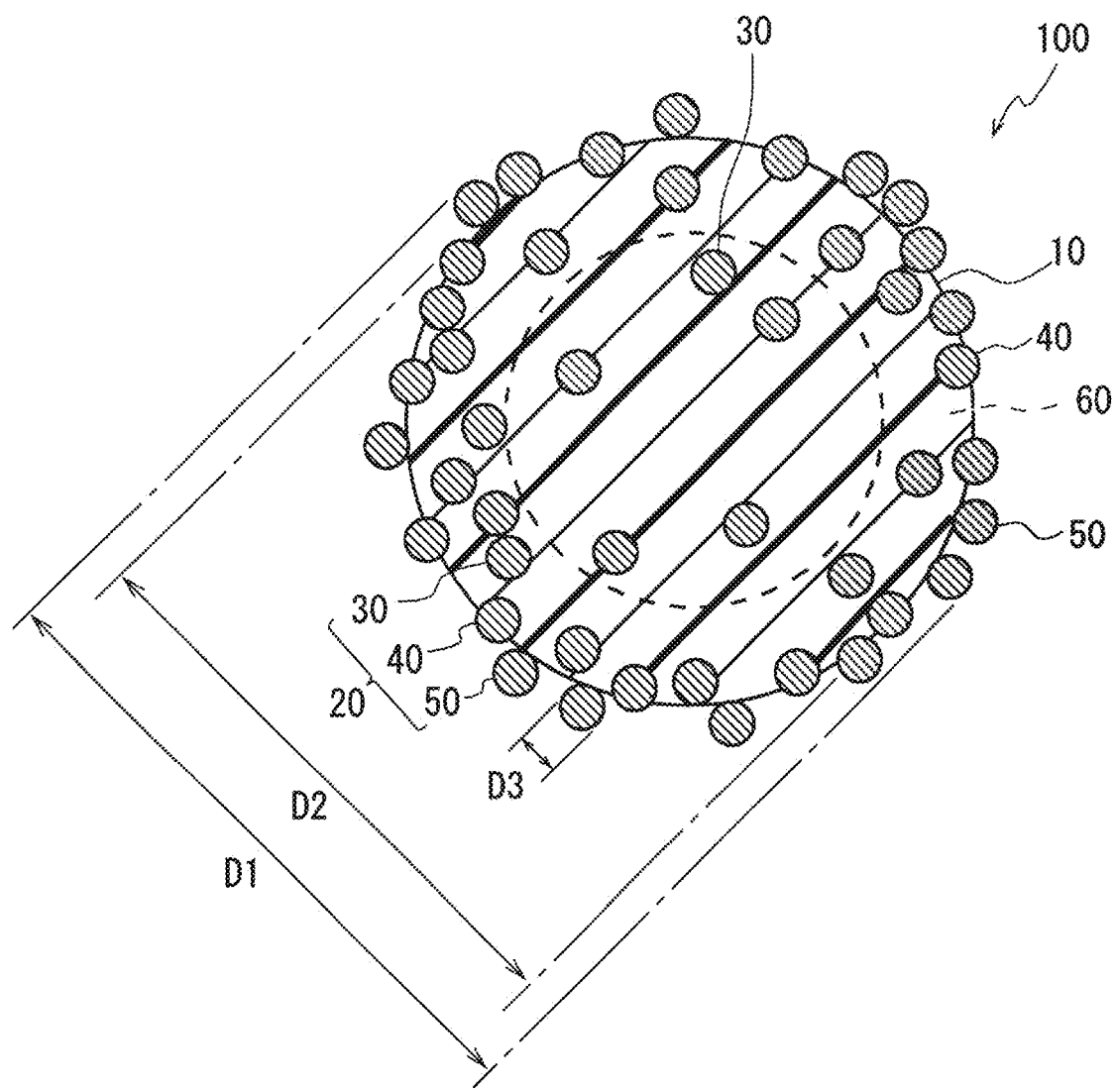
FIG. 1 is a schematic diagram showing a structure of a cross section of a resin-platinum composite according to an embodiment of the present invention.

Embodiments of the present invention will be appropriately described below in detail with reference to the drawings. FIG. 1 is a cross-sectional schematic diagram of a resin-platinum composite according to an embodiment of the present invention. A resin-platinum composite 100 includes a resin particle 10 and platinum particles 20. In the resin-platinum composite 100, the platinum particles 20 are fixed to the resin particle 10. The resin particle 10 is a particle that is relatively larger than the platinum particles 20. That is, in the resin-platinum composite 100, a plurality of platinum particles 20 that are relatively small are fixed to the large resin particle 10. As shown in FIG. 1, the relationships among a particle size D1 of the entire resin-platinum composite 100, a particle size D2 of the resin particle 10, and a particle size D3 of the platinum particles 20 are D1>D2>D3.

In addition, in the resin-platinum composite 100, some of the platinum particles 20 may be three-dimensionally distributed on a surface layer section 60 of the resin particle 10. In this case, some of the platinum particles 20 that are three-dimensionally distributed may be partially exposed to the outside of the resin particle 10 and the remaining platinum particles 20 may be enclosed in the resin particle 10. Specifically, as shown in FIG. 1, preferably, the platinum particles 20 include platinum particles that are completely enclosed in the resin particle 10 (hereinafter referred to as "enclosed particles 30"), platinum particles having a portion that is embedded in the resin particle 10 and a portion that is exposed to the outside of the resin particle 10 (hereinafter referred to as "partially exposed particles 40"), and platinum particles that are attached to the surface of the resin particle 10 (hereinafter referred to as "surface-attached particles 50").

For example, when the resin-platinum composite 100 is used as a labeling substance for immunological measurement or a reagent for immunological measurement, an antibody or antigen is fixed to the surface of the resin particle 10 or the surface of the partially exposed particles 40 or the surface-attached particles 50 and used. In this case, the antibody or antigen is fixed to the partially exposed particles 40 and the surface-attached particles 50, but it is not fixed to the enclosed particles 30. However, all of the partially exposed particles 40, the surface-attached particles 50 and the enclosed particles 30 exhibit light energy absorption due to electron transition in addition to localized surface plasmon resonance. Therefore, not only the partially exposed particles 40 and the surface-attached particles 50 but also the enclosed particles 30 contribute to improvement of visibility of a labeling substance for immunological measurement and a reagent for immunological measurement. Further, because the partially exposed particles 40 and the enclosed particles 30 have a larger area that is in contact with the resin particle 10 than the surface-attached particles 50 and exhibit an anchor effect due to the embedded state, they have a strong physical attachment force and are not easily detached from the resin particle 10. Therefore, the durability and stability of a labeling substance for immunological measurement and a reagent for immunological measurement using the resin-platinum composite 100 can be improved.

A case in which the resin-platinum composite 100 is applied as a labeling substance for immunological measurement (hereinafter simply referred to as a "labeling substance") or a reagent for immunological measurement (hereinafter simply referred to as a "reagent") will be exemplified below.

The entire surfaces of the enclosed particles 30 are covered with a resin constituting the resin particle 10. In addition, the surface area of the partially exposed particles 40 that is covered with the resin constituting the resin particle 10 is 5% or more and less than 100%. In consideration of the durability of a labeling substance for immunological measurement and a reagent for immunological measurement, a lower limit thereof is preferably 20% or more of the surface area and more preferably 30% or more thereof. In addition, the surface area of the surface-attached particles 50 that is covered with the resin constituting the resin particle 10 is preferably more than 0% and less than 5%.

In addition, an amount of the platinum particles 20 (a sum of the enclosed particles 30, the partially exposed particles 40, and the surface-attached particles 50) that is supported on the resin-platinum composite 100 is preferably 5 wt % to 70 wt % with respect to the weight of the resin-platinum composite 100. In such a range, the resin-platinum composite 100 is excellent in visibility, visual determination, and detection sensitivity as a labeling substance. When an amount of the platinum particles 20 supported thereon is less than 5 wt %, an amount of antibodies or antigens that are fixed is small, and detection sensitivity tends to decrease. An amount of the platinum particles 20 supported thereon is more preferably 15 wt % to 70 wt %, and most preferably 15 wt % to 60 wt %. Here, the resin-platinum composite 100 including the platinum particles 20 can have more excellent visibility, visual determination, and detection sensitivity as a labeling substance with a smaller supported amount compared to other metal particles (for example, a resin-gold composite including gold particles).

In addition, preferably, 10 wt % to 90 wt % of the platinum particles 20 are the partially exposed particles 40 and the surface-attached particles 50. In such a range, since an amount of antibodies or antigens fixed to the platinum particles 20 can be sufficiently ensured, the sensitivity as a labeling substance is high. More preferably, 20 wt % to 80 wt % of the platinum particles 20 are the partially exposed particles 40 and the surface-attached particles 50, and in consideration of the durability of a labeling substance for immunological measurement and a reagent for immunological measurement, most preferably, the surface-attached particles 50 make up 20 wt % or less.

In addition, when the resin-platinum composite 100 is used for immunological measurement, in order to obtain excellent detection sensitivity, 60 wt % to 100 wt %, preferably 75 to 100 wt %, and more preferably 85 to 100 wt % of the platinum particles 20 are in the surface layer section 60, and more preferably, may be in a range of 40% of the particle radius in the depth direction from the surface of the resin particle 10. In addition, when 5 wt % to 90 wt % of the platinum particles 20 in the surface layer section 60 are the partially exposed particles 40 or the surface-attached particles 50, an amount of antibodies or antigens fixed to the platinum particles 20 can be sufficiently ensured. This is preferable because the sensitivity as a labeling substance is high. In other words, 10 wt % to 95 wt % of the platinum particles 20 in the surface layer section 60 are preferably the enclosed particles 30.

Here, the "surface layer section" refers to a section in a range of 50% of the particle radius in the depth direction from the surface of the resin particle 10 based on the outmost position (that is, the protruding end of the partially exposed particles 40 or the surface-attached particles 50) of the resin-platinum composite 100. In addition, "distributed three-dimensionally" means that the platinum particles 20 are dispersed not only in the planar direction of the resin particle 10 but also in the depth direction.

Figure 2A:
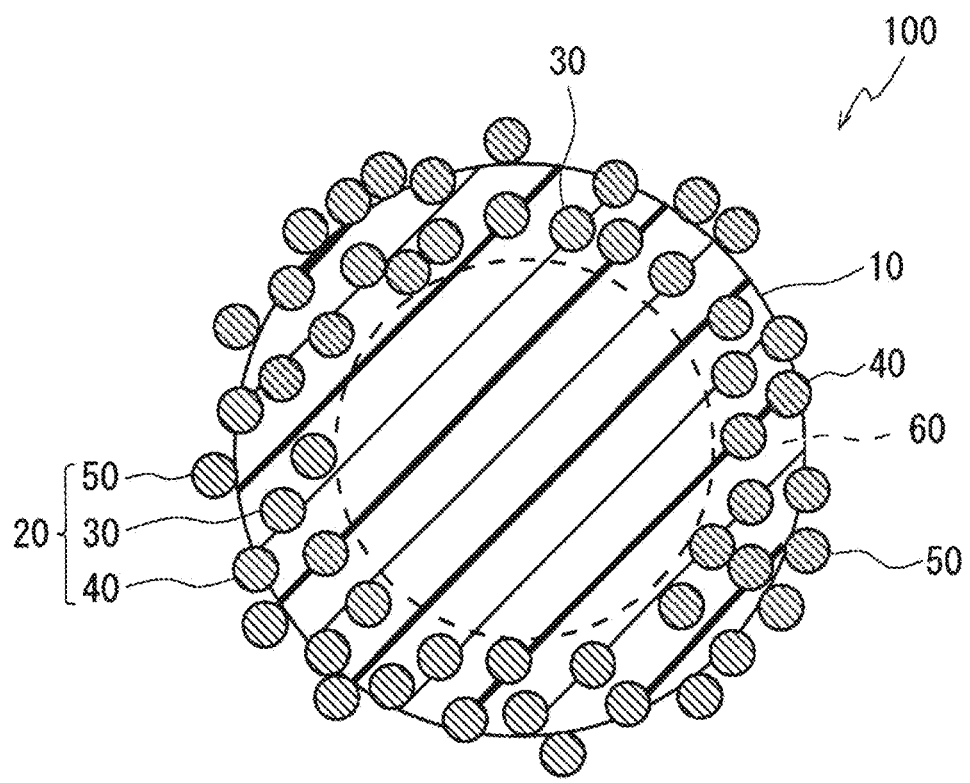
FIG. 2A is a schematic diagram showing a structure of a cross section of one embodiment of a resin-platinum composite.

As described above, since the enclosed particles 30 also exhibit light energy absorption due to electron transition in addition to localized surface plasmon resonance, not only the partially exposed particles 40 and the surface-attached particles 50 but also the enclosed particles 30 contribute to improvement of visibility of a labeling substance for immunological measurement and a reagent for immunological measurement. In consideration of such improvement of visibility, in the resin-platinum composite 100, for example, as shown in FIG. 2A, preferably, the enclosed particles 30 are concentratedly distributed in a certain range in the depth direction from the surface of the resin particle 10 and the enclosed particles 30 are not present near the center of the resin particle 10. More specifically, in order to effectively exhibit light energy absorption due to electron transition in addition to localized surface plasmon resonance by the enclosed particles 30, for example, when the particle size D2 of the resin particle 10 is 800 nm, 70 wt % or more, preferably 80 wt % or more, and more preferably 90 to 100 wt % of the enclosed particles 30 are in, for example, a range of 0 to 200 nm in the depth direction from the surface of the resin particle 10. In particular, when a region (enclosed particle distribution region) in which all of the enclosed particles 30 (100 wt %) are distributed is, for example, in a range of 0 to 100 nm from the surface of the resin particle 10, this is preferable because it is possible to maximize exhibition of light energy absorption due to electron transition in addition to localized surface plasmon resonance by the enclosed particles 30.

Figure 2B:
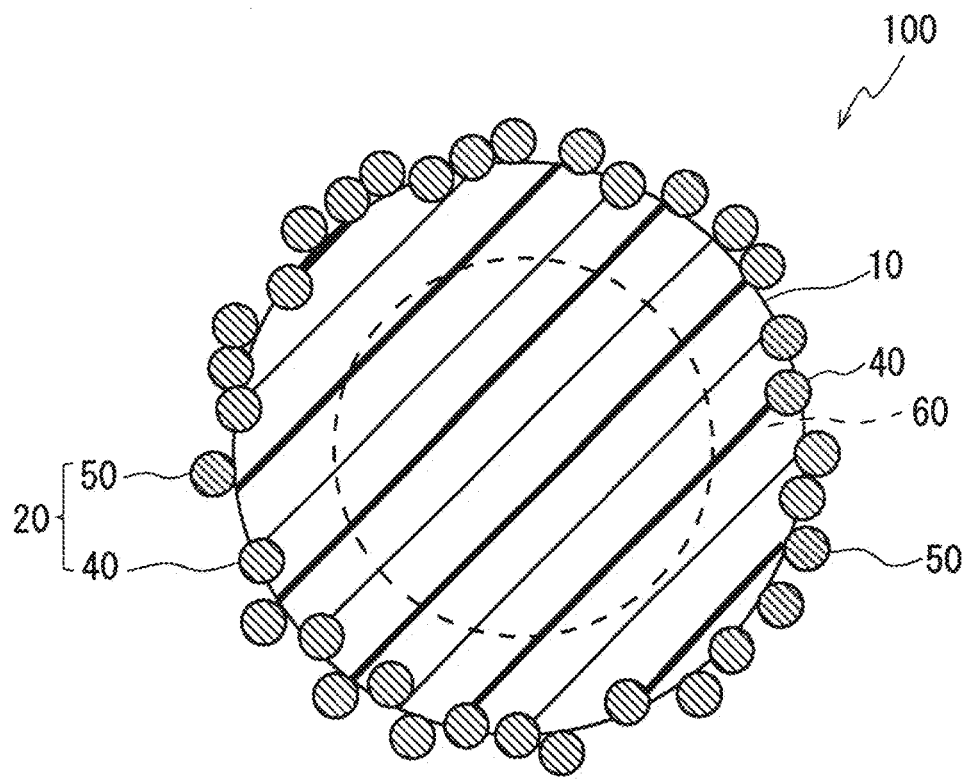
FIG. 2B is a schematic diagram showing a structure of a cross section of another embodiment of the resin-platinum composite.

In addition, the resin-platinum composite 100 may not include the enclosed particles 30. For example, as shown in FIG. 2B, in the resin-platinum composite 100, all of the platinum particles 20 may be fixed to the surface of the resin particle 10 without being superimposed in the radial direction of the resin particle 10. In this case, the platinum particles 20 include the partially exposed particles 40 and the surface-attached particles 50.

The resin particle 10 is preferably a polymer particle having a structure including a substituent to which platinum ions can be attached. In particular, a nitrogen-containing polymer particle is preferable. Since nitrogen atoms in the nitrogen-containing polymer allows anionic ions such as $[PtCl_6]^{2-}$ which are precursors of the platinum particles 20 that are excellent in visibility and to which antigens or antibodies are easily fixed to be easily chemically attached, they are preferable. In the present embodiment, in order to reduce platinum ions attached in the nitrogen-containing polymer to form the platinum particles 20, some of the generated platinum particles 20 become the enclosed particles 30 or the partially exposed particles 40. In addition, a polymer containing a carboxylic acid group such as an acrylic acid polymer and a polymer containing a sulfonic acid group such as polystyrene sulfonic acid (hereinafter collectively referred to as "a polymer to which cationic ions can be attached") allow a cationic ion such as $Pt^{2+}$ to be chemically attached due to the contained carboxylic acid group and sulfonic acid group, and thus are preferable. For example, when chemically attached $Pt^{2+}$ ions are reduced to form the platinum particles 20, it is possible to provide the same structure as that of the nitrogen-containing polymer particle. In addition, for example, since cationic ions which are precursors of a metal such as silver, nickel, or copper are easily attached and it is possible to prepare an alloy with platinum using the same, they are preferable.

On the other hand, in the case of resin particles other than the nitrogen-containing polymer having a structure including a substituent to which platinum ions can be attached, for example, polystyrene, it is difficult for the platinum ions to be attached to the inside of the resin. As a result, most of the generated platinum particles 20 become the surface-attached particles 50. As described above, the surface-attached particles 50 have a small area that is in contact with the resin particle 10, an adhesive strength between the resin and the metal is low, and an influence of detaching the platinum particles 20 from the resin particle 10 tends to be large.

The nitrogen-containing polymer is a resin including nitrogen atoms in the main chain or side chain, and is, for example, a polyamine, polyamide, polypeptide, polyurethane, polyurea, polyimide, polyimidazole, polyoxazole, polypyrrole, or polyaniline, and preferably, a polyamine such as poly-2-vinylpyridine, poly-3-vinylpyridine, and poly-4-vinylpyridine. In addition, when there is a nitrogen atom in the side chain, for example, an acrylic resin, a phenolic resin, and an epoxy resin can be widely used.

In addition, the polymer to which cationic ions can be attached is a resin including a carboxylic acid group, a sulfonic acid group, or the like in the main chain or side chain, and for example, polyacrylic acid, vinyl carboxylate, polyvinyl acetate, polyvinyl sulfonic acid, and polystyrene sulfonic acid can be widely used.

The nitrogen-containing polymer and the polymer to which cationic ions can be attached may be a copolymer with a known polymerizable monomer. Here, examples of the copolymer include a random copolymer, a block copolymer, an alternating copolymer, and a copolymer in which polymers are cross-linked. In addition, two or more types of monomers may be copolymerized to form the resin particle 10, and a monomer may be reacted with a functional group on the surface of the resin particle 10 and this may be further polymerized as a polymerizable active terminal. Although a copolymer composition thereof is not limited, there is preferably 10 mol % or more of a monomer including a substituent to which the platinum ions can be attached.

Compared to a resin composite including particles of other types of metals, the resin-platinum composite 100 including the platinum particles 20 is less likely to aggregate while it is bound to a ligand such as an antibody, and is remarkably excellent in dispersibility. In addition, the platinum particles 20 are resistant to changes such as oxidation and have excellent storage stability. Further, the platinum particles 20 exhibit absorption derived from localized surface plasmon resonance at a wavelength in, for example, a wide range of 250 nm to 900 nm, and also exhibit light energy absorption due to electron transition, and show strong development of a color close to black. Therefore, when the resin-platinum composite 100 is used as a labeling substance, high visibility is obtained in immunological measurement, and it is possible to increase detection sensitivity of an analyte. In this case, when the platinum particles 20 are used, excellent detection sensitivity can be obtained with a smaller supported amount than that of particles of another metal (for example, gold). Therefore, if the average particle size is the same, the resin-platinum composite 100 shows significantly higher detection sensitivity than a resin composite including particles of another type of metal.

The platinum particles 20 may include only platinum or may be an alloy including platinum and another metal. A platinum alloy refers to an alloy that includes platinum and a type of metal other than platinum and includes platinum at 1 weight % or more. Here, other types of metals that form an alloy with platinum are not particularly limited, and, for example, silver, nickel, copper, gold, and palladium are preferable, and gold and palladium having excellent storage stability and visibility are more preferable.

In addition, the average particle size of the platinum particles 20 (that is, an average of the particle sizes D3 in FIG. 1) measured by observation under a scanning electron microscope (SEM) is preferably, for example, 1 to 80 nm. When the average particle size of the platinum particles 20 is less than 1 nm or exceeds 80 nm, since localized surface plasmon resonance and light energy absorption due to electron transition are not easily exhibited, sensitivity tends to decrease. In order to obtain high detection sensitivity when the resin-platinum composite 100 is used for immunological measurement, the average particle size of the platinum particles 20 is preferably 1 nm or more and 50 nm or less, more preferably 1 nm or more and 30 nm or less, still more preferably 1 nm or more and 20 nm or less, and most preferably 1 nm or more and 15 nm or less. In particular, if the average particle size of the platinum particles 20 is 15 nm or less, when the resin-platinum composite 100 is used as a labeling substance for immunochromatography, particularly excellent detection sensitivity can be obtained.

In addition, the average particle size of the resin-platinum composite 100 (that is, an average of the particle sizes D1 in FIG. 1) is preferably, for example, 50 to 1000 nm. When the average particle size of the resin-platinum composite 100 is less than 50 nm, for example, since a supported amount of platinum particles tends to decrease, coloration tends to be weaker than that of platinum particles of the same size. If the average particle size of the resin-platinum composite 100 exceeds 1000 nm, when it is used as a labeling substance or a reagent, it is likely to clog pores in a chromatographic medium such as a membrane filter and the dispersibility tends to decrease. In order to improve the dispersibility when it is used as a labeling substance or a reagent, and obtain high detection sensitivity when the resin-platinum composite 100 is used for immunological measurement, the average particle size of the resin-platinum composite 100 is preferably 100 nm or more and 600 nm or less, more preferably 250 nm or more and 600 nm or less, and most preferably 300 nm or more and 600 nm or less. In particular, if the average particle size of the resin-platinum composite 100 is 300 nm or more, when the resin-platinum composite 100 is used as a labeling substance for immunochromatography, stable and excellent detection sensitivity can be obtained. Here, the particle size of the resin-platinum composite 100 is a value obtained by adding a length of the protrusion portion of the partially exposed particles 40 or the surface-attached particles 50 to a particle size of the resin particle 10 and can be measured by a laser diffraction and scattering method, a dynamic light scattering method, or a centrifugal sedimentation method.

[Method of Producing Resin-Platinum Composite]

A method of producing the resin-platinum composite 100 is not particularly limited. For example, a solution containing platinum ions is added to a dispersion of the resin particle 10 produced by an emulsion polymerization method, and the platinum ions are attached to the resin particle 10 (hereinafter referred to as a "platinum-ion-attached resin particle"). Further, when platinum-ion-attached resin particles are added to a reducing agent solution, the platinum ions are reduced, the platinum particles 20 are generated, and the resin-platinum composite 100 is obtained.

In addition, examples of the solution containing platinum ions include a chloroplatinic acid ($H_2PtCl_6$) aqueous solution, and a platinum chloride ($PtCl_2$) solution. In addition, a platinum composite may be used in place of platinum ions.

In addition, as a solvent for the solution containing platinum ions, in place of water, a hydrous alcohol such as methanol, ethanol, n-propanol, isopropanol, n-butanol, sec-butanol, and t-butanol, or an alcohol, and an acid such as hydrochloric acid, sulfuric acid, and nitric acid may be used.

In addition, as necessary, additives, for example, a water-soluble polymer compound such as polyvinyl alcohol, a surfactant, an alcohol; an ether such as tetrahydrofuran, diethyl ether, or diisopropyl ether; an alkylene glycol, an polyalkylene glycol, or a monoalkyl ether or dialkyl ether thereof, and a polyol such as glycerin; and various water-miscible organic solvents such as acetone and ketones, for example, methyl ethyl ketone, may be added to the solution. Such additives are effective in increasing a reduction reaction rate of platinum ions or controlling the size of the generated platinum particles 20.

In addition, a known substance can be used as the reducing agent. For example, sodium borohydride, dimethylamine borane, citric acid, sodium hypophosphite, hydrazine hydrate, hydrazine hydrochloride, hydrazine sulfate, formaldehyde, sucrose, glucose, ascorbic acid, erythorbic acid, sodium phosphinate, hydroquinone, and a rochelle salt may be exemplified. Among them, sodium borohydride, dimethylamine borane, and citric acid are preferable.

As necessary, a surfactant can be added to the reducing agent solution, and a pH of the solution can be adjusted. In order to adjust a pH, a buffer such as boric acid or phosphoric acid, an acid such as hydrochloric acid or sulfuric acid, and an alkali such as sodium hydroxide or potassium hydroxide can be used.

Moreover, when a reduction rate of platinum ions is adjusted according to the temperature of the reducing agent solution, the particle size of the generated platinum particles 20 can be controlled.

In addition, when platinum ions are reduced in the platinum-ion-attached resin particles and the platinum particles 20 are generated, the platinum-ion-attached resin particles may be added to the reducing agent solution, and the reducing agent may be added to the platinum-ion-attached resin particles. However, the former is preferable because the enclosed particles 30 and the partially exposed particles 40 are easily generated.

In addition, in order to maintain the dispersibility of the resin-platinum composite 100 in water, for example, citric acid, poly-L-lysine, polyvinyl pyrrolidone, polyvinyl pyridine, polyvinyl alcohol, or a dispersant such as DISPERBYK194, DISPERBYK180, and DISPERBYK184 (made by BYK-Chemie Japan) may be added.

In addition, a buffer such as boric acid or phosphoric acid, an acid such as hydrochloric acid or sulfuric acid, and an alkali such as sodium hydroxide or potassium hydroxide are used to adjust a pH, and the dispersibility can be maintained.

The resin-platinum composite 100 having the above configuration particularly allows antigens or antibodies to be attached to the surface of the platinum particles 20 and thus it can be preferably applied as a labeling substance for an immunological measurement method, for example, EIA, RIA, CLIA, FIA, LIA, PA, ICA, HA, and HI. In addition, in particular, it can be preferably applied as a material of a labeling substance for immunological measurement or a reagent for immunological measurement which is excellent in visual determination in a low concentration range (high sensitivity area). In addition, forms of a labeling substance for immunological measurement or a reagent for immunological measurement are not particularly limited. For example, a dispersion in which the resin-platinum composite 100 is dispersed in water or a buffer solution with an adjusted pH can be used.

A method of attaching antigens or antibodies to the surface of the platinum particles 20 is not particularly limited, and known physical attachment and chemical attachment methods can be used. For example, a physical attachment method in which the resin-platinum composite 100 is immersed in a buffer solution containing antigens or antibodies and incubated, and a chemical attachment method in which an SH group is introduced into antigens or antibodies and reacted with the resin-platinum composite 100 to form a Pt—SH bond may be exemplified. Among them, the chemical attachment method is preferable because the bond between the platinum particles 20 and antigens or antibodies is strong.

Next, a method of measuring an analyte in which the resin-platinum composite 100 is used as a labeling substance, a test strip for lateral flow chromatography, and an analyte detection and quantification kit will be described.

[Test Strip for Lateral Flow Chromatography]

Figure 3:
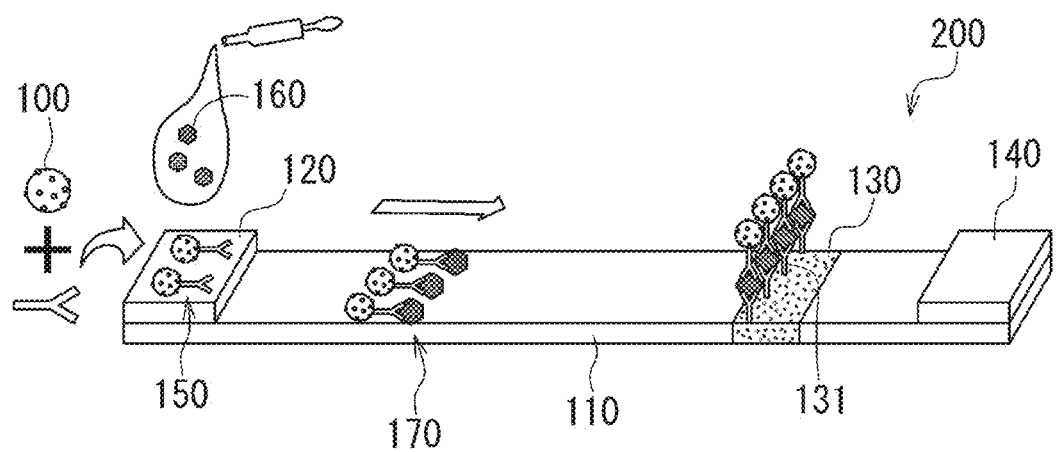
FIG. 3 is an explanatory diagram showing an overview of a method of measuring an analyte using a test strip for lateral flow chromatography according to an embodiment of the present invention.

First, a test strip for lateral flow chromatography (hereinafter simply referred to as a "test strip") according to an embodiment of the present invention will be described with reference to FIG. 3. As will be described below, a test strip 200 can be preferably used for a method of measuring an analyte according to an embodiment of the present invention.

The test strip 200 includes a membrane 110. On the membrane 110, a sample addition section 120, a determination section 130 and a liquid absorbing section 140 are provided in order in a development direction of a sample.

<Membrane>

As the membrane 110 used for the test strip 200, those used as membrane materials in general test strips can be applied. The membrane 110 exhibits, for example, a capillary action, and includes an inactive substance (an analyte 160, a substance that does not react with various ligands) made of a microporous material so that a sample is developed at the same time as the sample is added. Specific examples of the membrane 110 include a fibrous or nonwoven fibrous matrix, film, filter paper, glass fiber filter paper, cloth, and cotton made of polyurethane, polyester, polyethylene, polyvinyl chloride, polyvinylidene fluoride, nylon, or cellulose derivatives. Among them, a film, filter paper, glass fiber filter paper, and the like made of cellulose derivatives or nylon are preferably used. A nitrocellulose film, a mixed nitrocellulose ester (a mixture containing nitrocellulose and cellulose acetate) film, a nylon film, filter paper, and the like are more preferably used.

In order for a simpler operation, the test strip 200 preferably includes a support that supports the membrane 110. As the support, for example, a plastic can be used.

<Sample Addition Section>

The test strip 200 may include the sample addition section 120 configured to add a sample containing the analyte 160. The sample addition section 120 is a section for receiving the sample containing the analyte 160 on the test strip 200. The sample addition section 120 may be formed on the membrane 110 upstream from the determination section 130 in a direction in which the sample is developed. Alternatively, a sample addition pad made of a material such as cellulose filter paper, glass fibers, polyurethane, polyacetate, cellulose acetate, nylon, or cotton cloth may be provided on the membrane 110 to form the sample addition section 120.

<Determination Section>

A capture ligand 131 that specifically binds to the analyte 160 is fixed to the determination section 130. The capture ligand 131 can be used without particular limitation as long as it forms a specific bond with the analyte 160, and, for example, an antibody for the analyte 160 can be preferably used. Even if the sample is provided on the test strip 200, the capture ligand 131 is immobilized so that it cannot move from the determination section 130. The capture ligand 131 may be directly or indirectly fixed to the membrane 110 by physical or chemical bonding or attachment, or the like.

In addition, a configuration of the determination section 130 is not particularly limited as long as a composite 170 including a labeled antibody 150 and the analyte 160 comes in contact with the capture ligand 131 that specifically binds to the analyte 160. For example, the capture ligand 131 may be directly fixed to the membrane 110, and alternatively, the capture ligand 131 may be fixed to a pad made of cellulose filter paper, glass fibers, a nonwoven fabric, or the like fixed to the membrane 110.

<Liquid Absorbing Section>

The liquid absorbing section 140 is formed by a pad of a water-absorbing material, for example, cellulose filter paper, a nonwoven fabric, cloth, or cellulose acetate. A movement speed of the sample after a development front line (front line) of the added sample reaches the liquid absorbing section 140 varies depending on the material and size of the liquid absorbing section 140. Therefore, when the material and size of the liquid absorbing section 140 are selected, it is possible to set an optimal speed for detection and quantification of the analyte 160. Here, the liquid absorbing section 140 has an arbitrary configuration and may be omitted.

As necessary, the test strip 200 may further include an arbitrary unit such as a reaction section and a control section.

<Reaction Section>

Although not shown, in the test strip 200, a reaction section including the labeled antibody 150 may be formed on the membrane 110. The reaction section can be provided upstream from the determination section 130 in a direction in which the sample moves. Here, the sample addition section 120 in FIG. 3 may be used as a reaction section. When the test strip 200 includes the reaction section, if the sample containing the analyte 160 is supplied to the reaction section or the sample addition section 120, the analyte 160 contained in the sample and the labeled antibody 150 can be brought into contact with each other in the reaction section. In this case, when the sample is simply supplied to the reaction section or the sample addition section 120, since it is possible to form the composite 170 including the analyte 160 and the labeled antibody 150, so-called one step type immunochromatography is possible.

The reaction section is not particularly limited as long as it includes the labeled antibody 150 that specifically binds to the analyte 160. The labeled antibody 150 may be directly applied to the membrane 110. Alternatively, the reaction section may be a section in which the labeled antibody 150 is impregnated into a pad (conjugate pad) made of, for example, cellulose filter paper, glass fibers, or a nonwoven fabric and which is fixed to the membrane 110.

<Control Section>

Although not shown, in the test strip 200, a control section in which the capture ligand that specifically binds to the labeled antibody 150 is fixed may be formed on the membrane 110 in the direction in which the sample is developed. A color development intensity is measured in the determination section 130 and also the control section. Therefore, the sample supplied to the test strip 200 is developed and reaches the reaction section and the determination section 130, and it is possible to confirm that an examination has been performed normally. Here, the control section is produced in the same manner as the above-described determination section 130 except that another type of capture ligand that specifically binds to the labeled antibody 150 is used in place of the capture ligand 131, and can have the same configuration

[Method of Measuring Analyte]

Next, a method of measuring the analyte 160 according to an embodiment of the present invention that is performed using the test strip 200 will be described.

The method of measuring the analyte 160 of the present embodiment is a method of measuring the analyte 160 in which the analyte 160 contained in the sample is detected or quantified. In the method of measuring the analyte 160 of the present embodiment, the test strip 200 including the membrane 110 and the determination section 130 to which the capture ligand 131 that specifically binds to the analyte 160 is fixed in the membrane 110 is used. Here, the method of measuring the analyte 160 of the present embodiment can include the following processes (I) to (III):

Process (I): a process of contacting the analyte 160 contained in the sample with a labeled antibody 150 obtained by labeling an antibody that specifically binds to the analyte 160 with the resin-platinum composite 100 having a structure in which the plurality of platinum particles 20 are fixed to the resin particle 10;

Process (II): a process of contacting the composite 170 including the analyte 160 and the labeled antibody 150 formed in Process (I) with the capture ligand 131 in the determination section 130;

Process (III): a process of measuring a color development intensity derived from localized surface plasmon resonance and light energy absorption due to electron transition of the resin-platinum composite 100.

Process (I):

Process (I) is a process in which the analyte 160 contained in the sample is brought into contact with the labeled antibody 150. A contact mode is not particularly limited as long as the composite 170 including the analyte 160 and the labeled antibody 150 is formed. For example, the sample may be supplied to the sample addition section 120 or the reaction section (not shown) of the test strip 200, and the analyte 160 may be brought into contact with the labeled antibody in the reaction section, or the analyte 160 in the sample may be brought into contact with the labeled antibody 150 before the sample is supplied to the test strip 200.

The composite 170 formed in Process (I) is developed on the test strip 200 and moves and reaches the determination section 130.

Process (II):

In Process (II), in the determination section 130 of the test strip 200, the composite 170 including the analyte 160 and the labeled antibody 150 formed in Process (I) is brought into contact with the capture ligand 131. When the composite 170 is brought into contact with the capture ligand 131, the capture ligand 131 specifically binds to the analyte 160 of the composite 170. As a result, the composite 170 is captured in the determination section 130.

Here, since the capture ligand 131 does not specifically bind to the labeled antibody 150, when the labeled antibody 150 unbound with the analyte 160 reaches the determination section 130, the labeled antibody 150 unbound with the analyte 160 passes through the determination section 130. Here, when a control section (not shown) in which another capture ligand that specifically binds to the labeled antibody 150 is fixed is formed in the test strip 200, the labeled antibody 150 that has passed through the determination section 130 continues development, and binds to the other capture ligand in the control section. As a result, the labeled antibody 150 that does not form the composite 170 with the analyte 160 is captured in the control section.

After Process (II), as necessary, before Process (III), a washing process in which the test strip 200 is washed with a buffer solution that is generally used for a biochemical test, for example, water, physiological saline, or a phosphate buffer solution, may be performed. In the washing process, it is possible to remove the labeled antibody 150 (the labeled antibody 150 that is not bound to the analyte 160 and does not form the composite 170) that is not captured in the determination section 130, or the determination section 130 and the control section.

When the washing process is performed, in Process (III), if color development according to localized surface plasmon resonance and light energy absorption due to electron transition of the resin-platinum composite 100 in the determination section 130, or the determination section 130 and the control section is measured, it is possible to reduce a color development intensity of the background, and it is possible to increase a signal/background ratio. Therefore, it is possible to further improve detection sensitivity and quantitativeness.

Process (III):

Process (III) is a process in which a color development intensity derived from localized surface plasmon resonance and light energy absorption due to electron transition of the resin-platinum composite 100 is measured. In Process (II) or after the washing process is performed as necessary, in the test strip 200, a color development intensity derived from localized surface plasmon resonance and light energy absorption due to electron transition of the resin-platinum composite 100 is measured.

Here, when the control section is formed in the test strip 200, in Process (II), a composite in which the labeled antibody 150 is captured by another capture ligand is formed in the control section. Therefore, in Process (III), in the test strip 200, color development according to localized surface plasmon resonance and light energy absorption due to electron transition can occur not only in the determination section 130, but also in the control section. In this manner, a color development intensity is measured in the determination section 130 and also in the control section, and it is possible to confirm whether the sample supplied to the test strip 200 is developed normally and has reached the reaction section and the determination section 130.

<Sample and Analyte>

The sample used in the method of measuring an analyte of the present embodiment is not particularly limited as long as it includes a substance that may be an antigen such as a protein as the analyte 160. For example, a biological sample including the target analyte 160 (that is, whole blood, serum, plasma, urine, saliva, sputum, a liquid wiped from the nasal cavity or pharynx, a spinal fluid, an amniotic fluid, a papillary secretion, tears, sweat, exudate from skin, fluid extracted from tissues, cells, and feces), a food extract fluid, and the like are exemplified. As necessary, the analyte 160 contained in the sample may be pretreated before the above Process (I) in order to facilitate a specific binding reaction of the labeled antibody 150 and the capture ligand 131 with the analyte 160. Here, as the pretreatment, a chemical treatment using various chemicals such as an acid, a base, and a surfactant, and a physical treatment using heating, stirring, and ultrasonic waves are exemplified. In particular, when the analyte 160 is a substance such as an influenza virus NP antigen which is generally not exposed to the surface, a treatment using a surfactant or the like is preferably performed. As a surfactant used for this purpose, a nonionic surfactant can be used in consideration of a specific binding reaction, for example, a binding reactivity between the capture ligand 131 and the analyte 160 such as an antigen-antibody reaction.

In addition, the sample may be appropriately diluted with a solvent (such as water, physiological saline, or a buffer solution) or a water-miscible organic solvent which is used for a general immunological analysis method.

As the analyte 160, for example, a tumor marker, a signal transmission substance, a protein (including polypeptides, oligopeptides, and the like), nucleic acid (including single- or double-stranded DNA and RNA, polynucleotides, oligo-nucleotides, PNA (peptide nucleic acid), and the like) such as a hormone, a substance including a nucleic acid, sugars (including oligosaccharides, polysaccharides, carbohydrates, and the like), a substance including a carbohydrate, and other molecules such as a liquid are exemplified. The analyte 160 is not particularly limited as long as it specifically binds to the labeled antibody 150 and the capture ligand 131. For example, a carcinoembryonic antigen (CEA), an HER2 protein, a prostate specific antigen (PSA), CA19-9, α-fetoprotein (AFP), an immunosuppressive acidic protein (IAP), CA15-3, CA125, an estrogen receptor, a progesterone receptor, fecal occult blood, troponin I, troponin T, CK-MB, CRP, human chorionic gonadotropin (HCG), luteinizing hormone (LH), follicle stimulating hormone (FSH), a syphilis antibody, an influenza virus human hemoglobin, a chlamydial antigen, an A group β *streptococcus* antigen, an HBs antibody, an HBs antigen, rotavirus, adenovirus, albumin, and glycated albumin are exemplified. Among them, an antigen that is solubilized by a nonionic surfactant is preferable, and an antigen that forms a self-assembly such as a virus nuclear protein is more preferable.

<Labeled Antibody>

In Process (I), the labeled antibody 150 is brought into contact with the analyte 160 contained in the sample, and is used to form the composite 170 including the analyte 160 and the labeled antibody 150. The labeled antibody 150 is obtained by labeling an antibody that specifically binds to the analyte 160 with the resin-platinum composite 100 having a structure in which the plurality of platinum particles 20 are fixed to the resin particle 10. Here, "labeling" means that the resin-platinum composite 100 is directly or indirectly fixed to an antibody by chemical or physical binding or attachment so that the resin-platinum composite 100 is not detached from the labeled antibody 150 in Processes (I) to (III). For example, the labeled antibody 150 may be a substance in which the resin-platinum composite 100 directly binds to an antibody or a substance in which an antibody and the resin-platinum composite 100 are bound by an arbitrary linker molecule or they are fixed to insoluble particles.

In addition, in the present embodiment, the "antibody" is not particularly limited. For example, a polyclonal antibody, a monoclonal antibody, and an antibody obtained by genetic recombination, and antibody fragments [for example, H chain, L chain, Fab, and F(ab')$_2$] having an ability to bind to an antigen and the like can be used. In addition, any of IgG, IgM, IgA, IgE, and IgD may be used as immunoglobulin. An animal species that produces an antibody may be a human or a non-human animal (for example, a mouse, rat, rabbit, goat, or horse). Specific examples of the antibody include an anti-PSA antibody, an anti-AFP antibody, an anti-CEA antibody, an anti-adenovirus antibody, an anti-influenza virus antibody, an anti-HCV antibody, an anti-IgG antibody, and an anti-human IgE antibody.

<Preferable Method of Producing Labeled Antibody>

Next, a preferable method of producing the labeled antibody 150 will be described. Production of the labeled antibody 150 can include at least the next process A;

process A) a process in which the resin-platinum composite 100 is mixed with and bound to an antibody under a first pH condition to obtain the labeled antibody 150, and preferably further includes process B;

process B) a process in which the labeled antibody 150 is treated under a second pH condition.

[Process A]

In the process A, the resin-platinum composite 100 is mixed with an antibody under a first pH condition to obtain the labeled antibody 150. In process A, preferably, the solid resin-platinum composite 100 that is dispersed in a liquid phase is brought into contact with an antibody.

In order for the resin-platinum composite 100 to be uniformly brought into contact with an antibody while dispersion of the resin-platinum composite 100 and the activity of the antibody are maintained, the first pH condition is preferably a pH condition in a range of 2 to 10 and, for example, more preferably a pH condition in a range of 5 to 9. When a pH condition for binding the resin-platinum composite 100 and the antibody is less than 2, the antibody may be denatured and inactivated due to strong acidity. When a pH exceeds 10, the resin-platinum composite 100 and the antibody aggregate and are not easily dispersed when mixed. However, when the antibody is not inactivated due to strong acidity, a treatment is possible even at a pH below 2.

The process A is preferably performed in a binding buffer solution (binding buffer) adjusted to the first pH condition. For example, a predetermined amount of the resin-platinum composite 100 is mixed into a binding buffer solution adjusted to the above pH and mixed sufficiently. As the binding buffer solution, for example, a boric acid solution adjusted to a predetermined concentration can be used. A pH of the binding buffer solution can be adjusted using, for example, hydrochloric acid, sodium hydroxide, or the like.

Next, when a predetermined amount of antibody is added to the obtained mixed solution and the solution is sufficiently stirred and mixed, it is possible to obtain a labeled antibody-containing solution. From the labeled antibody-containing solution obtained in this manner, only the labeled antibodies 150 forming a solid portion can be separated using a solid and liquid separation method, for example, centrifugation.

[Process B]

In the process B, the labeled antibody 150 obtained in the process A is treated under a second pH condition, and blocking is performed to prevent non-specific attachment to the labeled antibody 150. In this case, the labeled antibody 150 separated by the solid and liquid separation method is dispersed in a liquid phase under the second pH condition.

In order to maintain the activity of the antibody and prevent the labeled antibodies 150 from aggregating, the second pH condition is preferably in a range of, for example, a pH of 2 to 10. In order to prevent non-specific attachment of the labeled antibody 150, a pH is more preferably in a range of 5 to 9. When a blocking condition is a pH below 2, the antibody may be denatured and inactivated due to strong acidity. When a pH exceeds 10, the labeled antibodies 150 aggregate and are not easily dispersed.

The process B is preferably performed using a blocking buffer solution (Blocking Buffer) adjusted to the second pH condition. For example, the blocking buffer solution adjusted to the above pH is added to a predetermined amount of the labeled antibody 150, and the labeled antibodies 150 are uniformly dispersed in the blocking buffer solution. As the blocking buffer solution, for example, a solution of a protein that does not bind to an object to be detected is preferably used. As the protein that can be used for the blocking buffer solution, for example, bovine serum albumin, ovalbumin, casein, and gelatin can be exemplified. More specifically, a bovine serum albumin solution adjusted to a predetermined concentration can be preferably used. A pH of the blocking buffer solution can be adjusted using, for example, hydrochloric acid, sodium hydroxide, or the like. When the labeled antibodies 150 are dispersed, for example, a dispersion method such as an ultrasonic treatment is preferably used. Accordingly, a dispersion in which the labeled antibodies 150 are uniformly dispersed is obtained.

In the above process A and process B, the resin-platinum composites 100 including the platinum particles 20 are unlikely to aggregate due to pH, and can be treated in a wide pH range from acidic to alkaline. On the other hand, for example, in a resin-gold composite including gold particles, in the process A, under a condition of a pH above 7, resin-gold composites tend to aggregate, and in the process B, under a condition of a pH above 9, the resin-gold composites tend to aggregate. Therefore, the resin-platinum composite 100 used in the present invention has an advantage that it is not easily limited by conditions for producing labeled antibodies.

As described above, the dispersion of the labeled antibody 150 is obtained. Only the labeled antibodies 150 forming a solid portion can be separated using a solid and liquid separation method, for example, centrifugation, from the dispersion. In addition, as necessary, a washing treatment and a storage treatment can be performed. The washing treatment and the storage treatment will be described below.

(Washing Treatment)

In the washing treatment, a washing buffer solution is added to the labeled antibodies 150 separated using the solid and liquid separation method, and the labeled antibodies 150 are uniformly dispersed in the washing buffer solution. For dispersion, for example, a dispersion method such as an ultrasonic treatment is preferably used. The washing buffer solution is not particularly limited. For example, a tris buffer solution, glycinamide buffer solution, and arginine buffer solution with a predetermined concentration adjusted to be in a range of a pH of 8 to 9 can be used. A pH of the washing buffer solution can be adjusted using, for example, hydrochloric acid, sodium hydroxide, or the like. The washing treatment of the labeled antibody 150 can be performed a plurality of times as necessary.

(Storage Treatment)

In the storage treatment, a storage buffer solution is added to the labeled antibodies 150 separated using a solid and liquid separation method and the labeled antibodies 150 are uniformly dispersed in the storage buffer solution. For dispersion, for example, a dispersion method such as an ultrasonic treatment is preferably used. As the storage buffer solution, for example, a solution obtained by adding an aggregate inhibitor and/or stabilizer with a predetermined concentration to a washing buffer solution can be used. As the aggregate inhibitor, for example, sugars represented by sucrose, maltose, lactose, and trehalose and polyhydric alcohols represented by glycerin and a polyvinyl alcohol can be used. The stabilizer is not particularly limited. For example, proteins such as bovine serum albumin, ovalbumin, casein, and gelatin can be used. In this manner, the storage treatment of the labeled antibody 150 can be performed.

In the above-described processes, additionally, as necessary, a surfactant and a preservative such as sodium azide and a paraoxybenzoic acid ester can be used.

[Analyte Measurement Kit]

The analyte measurement kit according to an embodiment of the present invention is a kit for detecting or quantifying the analyte 160 contained in the sample based on, for example, a method of measuring an analyte of the present embodiment using the test strip 200.

The analyte measurement kit of the present embodiment includes the membrane 110, the test strip 200 including the determination section 130 in which the capture ligand 131 that specifically binds to the analyte 160 is fixed in the membrane 110, and a detection reagent including the labeled antibody 150 obtained by labeling an antibody that specifically binds to the analyte 160 with the resin-platinum composite 100 having a structure in which the plurality of platinum particles 20 are fixed to the resin particle 10. The analyte measurement kit of the present embodiment may further include other components as necessary.

When the analyte measurement kit according to the present embodiment is used, after Process (I) in which the analyte 160 in the sample is brought into contact with the labeled antibody 150 in the detection reagent is performed, the sample is supplied to the reaction section of the test strip 200 or the sample addition section 120, and Process (II) and Process (III) may be sequentially performed. Alternatively, the detection reagent is applied upstream from the determination section 130 of the test strip 200 and is appropriately dried, the reaction section is formed, the sample is then added to the formed reaction section or a position (for example, the sample addition section 120) upstream from the reaction section, and Processes (I) to (III) may be sequentially performed.

EXAMPLES

Next, the present invention will be described in detail with reference to examples, but the present invention is not limited to such examples. Unless otherwise particularly mentioned in the following examples and comparative examples, various measurements and evaluations are as follows.

<Measurement of Absorbance of Resin-Metal Composite>

The absorbance of the resin-metal composite was measured by putting a resin-metal composite dispersion (dispersion medium: water) prepared to 0.01 wt % into an optical white plate glass cell (optical path length of 10 mM), and measuring the absorbance at 570 nm for gold and at 700 nm for platinum using an instant multi-channel photometric system (MCPD-3700 made by OTSUKA Electronics Co., Ltd.). In the case of gold, when the absorbance at 570 nm was 0.9 or more, it was determined as A (favorable), when the absorbance at 570 nm was 0.5 to less than 0.9, it was determined as B (acceptable), and when the absorbance at 570 nm was less than 0.5, it was determined as C (not acceptable). In the case of platinum, when the absorbance at 700 nm was 0.6 or more, it was determined as A (favorable), when the absorbance at 700 nm was 0.1 to less than 0.6, it was determined as B (acceptable), and when the absorbance at 700 nm was less than 0.1, it was determined as C (not acceptable). Here, a colored latex was evaluated based on the same criteria as the gold and platinum.

<Measurement of Concentration of Solid Content and Measurement of Supported Amount of Metal>

1 g of the dispersion whose concentration was not adjusted was put into a ceramic crucible, and was subjected to a heat treatment at 70° C. for 3 hours. The weights before and after the heat treatment were measured and the concentration of the solid content was calculated by the following formula.

Concentration of solid content (wt %)=[weight (g) after drying/weight (g) before drying]×100

In addition, the sample after the heat treatment was additionally subjected to a heat treatment at 500° C. for 5 hours, the weights before and after the heat treatment were measured, and a supported amount of a metal was calculated by the following formula.

Supported amount of metal (wt %)=[weight (g) after heat treatment at 500° C./weight (g) before heat treatment at 500° C.]×100

<Measurement of Average Particle Size of Resin-Metal Composite>

A disk centrifugal particle size distribution measurement device (CPS Disc Centrifuge DC24000 UHR, made by CPS Instruments, Inc.) was used for measurement. The measurement was performed while the resin-metal composites were dispersed in water.

<Evaluation by Immunochromatography>

Using the dispersion of resin-metal composite-labeled antibodies produced in the examples and the like, measurement was performed according to the following immunochromatography, and the performance of the resin-metal composite dispersion was evaluated.

(Evaluation Method)

A monochrome screen for influenza type A evaluation (made by Adtec Co.) was used for evaluation. Color development levels after 5 minutes, after 10 minutes, and after 15 minutes were compared. In performance evaluation, for antigens, two-fold serial dilutions (1-fold to 1024-fold) of an influenza type A positive control (APC) were used (the concentration of virus before APC dilution was 5000 FFU/ml).

(Evaluation Procedure)

3 μL of the resin-metal composite-labeled antibody dispersion was put into each well of a 96-well plate, and 100 μL of two-fold serial dilutions (1-fold to 1024-fold) of the APC and 100 μL of a negative control were mixed. Next, 50 μL of the result was added to a monochrome screen for influenza type A evaluation, and color development levels were evaluated after 5 minutes, after 10 minutes, and after 15 minutes. The color development level was determined using a color sample for gold colloid determination (made by Adtec Co.).

<Measurement of Average Particle Size of Metal Particles>

An average particle size of metal particles was measured as follows. The area average size of metal particles was measured from an image of a substrate produced by adding a resin-metal composite dispersion dropwise to a metallic mesh with a carbon support film observed under a field emission scanning electron microscope (STEM; SU-9000 made by Hitachi High-Technologies Corporation).

<Dispersibility Evaluation>

A binding buffer solution (0.9 mL) was added to a 1 wt % resin-metal composite (0.1 mL) and sufficiently mixed. In addition, 100 μg of anti-influenza type A monoclonal antibody was added thereto, and turned and stirred at room temperature for 3 hours, and the dispersibility of the obtained resin-metal composite-labeled antibody was visually determined. Evaluation was performed with three types of binding buffer solutions.

Binding buffer solution a: 100 mM boric acid solution was adjusted to pH≈3 with HCl.

Binding buffer solution b: 100 mM boric acid solution pH≈6.5

Binding buffer solution c: 100 mM boric acid solution was adjusted to pH≈8.5 with NaOH.

Figure 4:
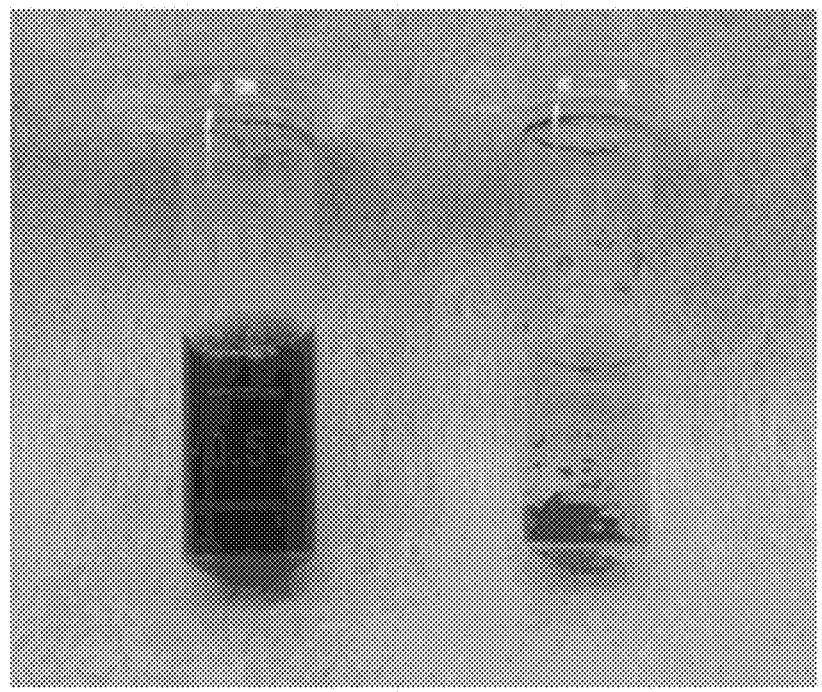
FIG. 4 is a picture showing an example of results of dispersibility evaluation of a resin-metal composite-labeled antibody.

The dispersibility was determined as follows. When the resin-metal composite-labeled antibodies did not aggregate and did not sediment, it was determined as A (favorable), and when the resin-metal composite-labeled antibodies aggregated and sedimented, it was determined as C (not acceptable). A dispersibility evaluation example is shown in FIG. 4. In FIG. 4, the left side shows a state in which the resin-metal composite-labeled antibodies did not aggregate and did not sediment, and the right side shows a state in which the resin-metal composite-labeled antibodies aggregated and sedimented. Here, FIG. 4 shows states in consideration of results of resin-gold composite-labeled antibodies.

Example 1

<Synthesis of Resin Particles>

ALIQUAT® 336 [made by Aldrich Co.] (3.00 g) and polyethylene glycol methyl ether methacrylate (PEGMA, 10.00 g) were dissolved in 300 g of pure water, 2-vinylpyridine (2-VP, 49.50 g) and divinylbenzene (DVB, 0.50 g) were then added thereto, and stirred at 150 rpm and 30° C. for 50 minutes and then at 60° C. for 30 minutes under a nitrogen atmosphere. After the stirring, 2,2-azobis(2-methylpropionamidine)dihydrochloride (AIBA, 0.250 g) dissolved in 18.00 g of pure water was added dropwise for 2 minutes, and stirred at 150 rpm and 60° C. for 3.5 hours, and thus resin particles with an average particle size of 370 nm were obtained. An operation in which precipitation was performed by centrifugation (at 9000 rpm for 45 minutes), a supernatant was removed, and dispersion was then performed again in pure water was performed three times, and impurities were then removed by a dialysis treatment. Then, the concentration was adjusted and a 10 wt % resin particle dispersion was obtained.

245 ml of pure water was added to the resin particle dispersion (90 ml), a 400 mM chloroplatinic acid aqueous solution (90 ml) was then added thereto and the mixture was stirred at 60 rpm and 30° C. for 3 hours and then left at room temperature for 24 hours. Then, an operation in which the resin particles were precipitated by centrifugation (at 3100 rpm for 30 minutes) and a supernatant was removed was performed three times, and thus excess chloroplatinic acid was removed. Then, the concentration was adjusted and a dispersion with 5 wt % platinum-ion-attached resin particles was prepared.

Next, the dispersion with 5 wt % platinum-ion-attached resin particles (55 ml) was added to 3825 ml of pure water and a 132 mM dimethylamine borane aqueous solution (110 ml) was added dropwise for 20 minutes with stirring at 160 rpm and 3° C., and then stirred at 160 rpm and 3° C. for 1 hour. Then, the mixture was stirred at 160 rpm and 25° C. for 3 hours, and thus resin-platinum composites with an average particle size of 382 nm were obtained. An operation in which the resin-platinum composites were precipitated by centrifugation (at 3100 rpm for 60 minutes), a supernatant was removed, and dispersion was then performed again in pure water was performed three times, and impurities were then removed by purification according to a dialysis treatment. Then, the concentration was adjusted and a 1 wt % resin-platinum composite dispersion was obtained. The absorbance of the produced resin-platinum composite dispersion was measured according to the above method. The result was 0.70. In addition, the average particle size of the formed platinum particles was 5 nm, and the supported amount of platinum was 38.5 wt %. In the resin-platinum composite, the platinum particles included enclosed platinum particles that were completely enclosed in the resin particle, partially exposed platinum particles having a portion that was embedded in the resin particle and a portion that was exposed to the outside of the resin particle, and surface-attached platinum particles that were attached to the surface of the resin particle. At least some of the platinum particles were distributed three-dimensionally on the surface layer section of the resin particle.

Using the obtained resin-platinum composite, the dispersibility when the antibody was bound was evaluated according to the following "dispersibility evaluation." As a result, all of the binding buffer solutions a, b, and c were A. Therefore, in the following evaluation by immunochromatography, binding of influenza antibodies and blocking using bovine serum albumin were performed at a pH of 8.5 (binding buffer solution c).

<Evaluation by Immunochromatography>

100 μg of influenza antibody was mixed into 1 ml of the obtained resin-platinum composite dispersion (0.1 wt %) and stirred at room temperature for about 3 hours, and the antibody was bound to the resin-platinum composite. A bovine serum albumin solution was added so that the final concentration was 1% and stirred at room temperature for 2 hours, and the surface of the resin-platinum composite was blocked. Centrifugation was performed at 12000 rpm and 4° C. for 5 minutes for recovery, suspending in a buffer solution including 0.2% bovine serum albumin was performed, and a resin-platinum composite-labeled antibody dispersion was produced.

Using the produced resin-platinum composite-labeled antibody dispersion, performance of the resin-platinum composite dispersion was evaluated by performing measurement by immunochromatography. The results are shown below.

TABLE 1

| | | Slot No. | | | | | | | | | | | |
|---|---|---|---|---|---|---|---|---|---|---|---|---|---|
| | | 1 | 2 | 3 | 4 | 5 | 6 | 7 | 8 | 9 | 10 | 11 | 12 |
| Antigen dilution series | | APC × 1 | APC × 2 | APC × 4 | APC × 8 | APC × 16 | APC × 32 | APC × 64 | APC × 128 | APC × 256 | APC × 512 | APC × 1024 | Negative control |
| Color development level | After 5 minutes | 5.0 | 4.0 | 3.0 | 2.5 | 1.5 | 1.0 | 0.5 | 0.1 | 0.1 | 0 | 0 | 0 |
| | After 10 minutes | 6.0 | 5.0 | 4.0 | 3.5 | 2.5 | 2.0 | 1.0 | 0.5 | 0.5 | 0.1 | 0 | 0 |
| | After 15 minutes | 6.0 | 5.0 | 4.5 | 4.0 | 3.0 | 2.5 | 1.5 | 1.0 | 0.5 | 0.5 | 0.1 | 0 |

Based on the above Table 1, it was confirmed that the resin-platinum composite-labeled antibody exhibited favorable color development with respect to antigens diluted 512-fold.

Example 2

<Synthesis of Resin Particles>

ALIQUAT® 336 [made by Aldrich Co.] (1.50 g) and polyethylene glycol methyl ether methacrylate (PEGMA, 10.00 g) were dissolved in 300 g of pure water, 2-vinylpyridine (2-VP, 49.50 g) and divinylbenzene (DVB, 0.50 g) were then added thereto, and then stirred at 150 rpm and 30° C. for 50 minutes and then at 60° C. for 30 minutes under a nitrogen atmosphere. After the stirring, 2,2-azobis(2-methylpropionamidine)dihydrochloride (AIBA, 0.50 g) dissolved in 18.00 g of pure water was added dropwise for 2 minutes and stirred at 150 rpm and 60° C. for 3.5 hours, and thus resin particles with an average particle size of 430 nm were obtained. An operation in which precipitation was performed by centrifugation (at 9000 rpm for 45 minutes), a supernatant was removed, and dispersion was then performed again in pure water was performed three times, and impurities were then removed by a dialysis treatment. Then, the concentration was adjusted and a 10 wt % resin particle dispersion was obtained.

245 ml of pure water was added to the resin particle dispersion (90 ml), a 400 mM chloroplatinic acid aqueous solution (90 ml) was then added thereto and the mixture was stirred at 60 rpm and 30° C. for 3 hours and then left at room temperature for 24 hours. Then, an operation in which the resin particles were precipitated by centrifugation (at 3100 rpm for 30 minutes) and a supernatant was removed was performed three times, and thus an excess chloroplatinic acid was removed. Then, the concentration was adjusted and a dispersion with 5 wt % platinum ions-attached resin particles was prepared.

Figure 5:
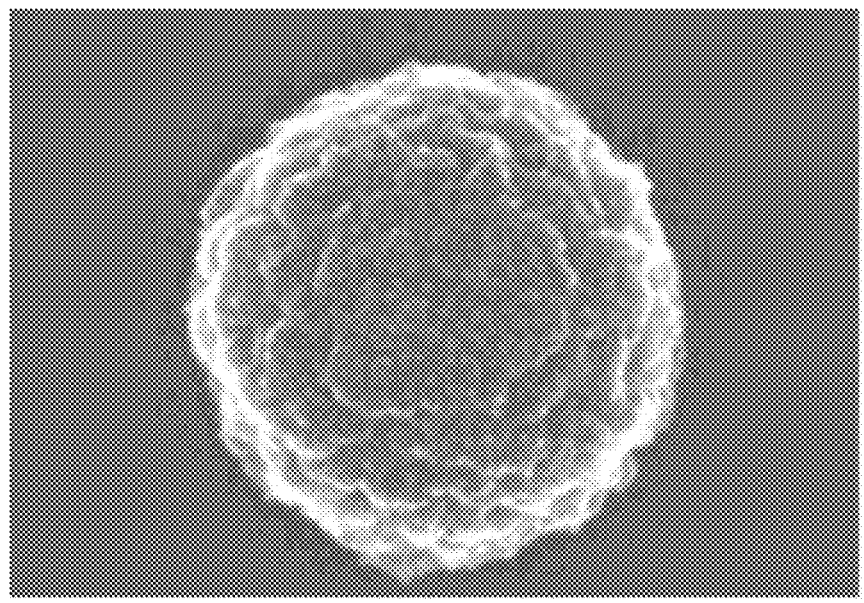
FIG. 5 is a scanning electron microscope (SEM) picture of a resin-platinum composite obtained in Example 2.
Figure 6:
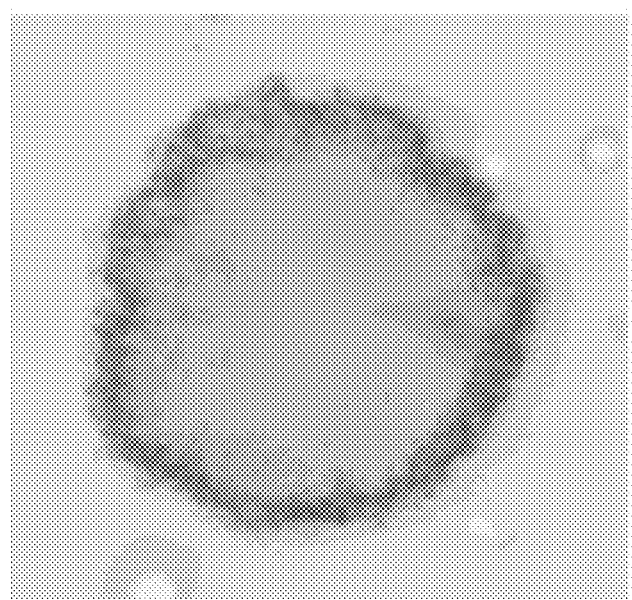
FIG. 6 is a scanning transmission electron microscope (STEM) picture of a cross section of the resin-platinum composite obtained in Example 2.

Next, the dispersion with 5 wt % platinum ions-attached resin particles (55 ml) was added to 3825 ml of pure water and a 132 mM dimethylamine borane aqueous solution (110 ml) was added dropwise for 20 minutes with stirring at 160 rpm and 3° C., and then stirred at 160 rpm and 3° C. for 1 hour. Then, the mixture was stirred at 160 rpm and 25° C. for 3 hours, and thus resin-platinum composites with an average particle size of 454 nm were obtained. An operation in which the resin-platinum composites were precipitated by centrifugation (at 3100 rpm for 60 minutes), a supernatant was removed, and dispersion was then performed again in pure water was performed three times and impurities were then removed by purification according to a dialysis treatment. Then, the concentration was adjusted and a 1 wt % resin-platinum composite dispersion was obtained. The absorbance of the produced resin-platinum composite dispersion was measured according to the above method. The result was 0.70. In addition, the average particle size of the formed platinum particles was 5 nm and the supported amount of platinum was 37.7 wt %. A scanning electron microscope (SEM) picture of the surface of the obtained resin-platinum composite is shown in FIG. 5, and a scanning transmission electron microscope (STEM) picture of a cross section thereof is shown in FIG. 6. In the resin-platinum composite, the platinum particles included enclosed platinum particles that were completely enclosed in the resin particle, partially exposed platinum particles having a portion that was embedded in the resin particle and a portion that was exposed to the outside of the resin particle, and surface-attached platinum particles that were attached to the surface of the resin particle. At least some of the platinum particles were distributed three-dimensionally on the surface layer section of the resin particle. Here, 98 wt % of the platinum particles were in a range of 40% of the particle radius in the depth direction from the surface of the resin particle.

Using the obtained resin-platinum composite, the dispersibility when the antibody was bound was evaluated according to the following "dispersibility evaluation." As a result, all of the binding buffer solutions a, b, and c were A. Therefore, in the following evaluation by immunochromatography, binding of influenza antibodies and blocking using bovine serum albumin were performed at a pH of 8.5 (binding buffer solution c).

<Evaluation by Immunochromatography>

A resin-platinum composite-labeled antibody dispersion was produced by performing the same operation as in Example 1.

Using the produced resin-platinum composite-labeled antibody dispersion, performance of the resin-platinum composite dispersion was evaluated by performing measurement by immunochromatography. The results are shown below.

TABLE 2

| | | Slot No. | | | | | | | | | | | |
|---|---|---|---|---|---|---|---|---|---|---|---|---|---|
| | | 1 | 2 | 3 | 4 | 5 | 6 | 7 | 8 | 9 | 10 | 11 | 12 |
| Antigen dilution series | | APC × 1 | APC × 2 | APC × 4 | APC × 8 | APC × 16 | APC × 32 | APC × 64 | APC × 128 | APC × 256 | APC × 512 | APC × 1024 | Negative control |
| Color development level | After 5 minutes | 6.0 | 5.0 | 4.0 | 3.0 | 2.5 | 1.5 | 1.0 | 0.5 | 0.5 | 0.1 | 0.1 | 0 |
| | After 10 minutes | 7.0 | 6.0 | 5.0 | 4.0 | 3.5 | 2.5 | 2.0 | 1.0 | 0.5 | 0.5 | 0.1 | 0 |
| | After 15 minutes | 7.0 | 6.0 | 5.0 | 4.0 | 3.5 | 3.0 | 2.0 | 1.5 | 1.0 | 0.5 | 0.5 | 0.1 |

Based on the above Table 2, it was confirmed that the resin-platinum composite-labeled antibody exhibited favorable color development with respect to antigens diluted 1024-fold.

Example 3

<Synthesis of Resin Particles>

ALIQUAT® 336 [made by Aldrich Co.] (2.00 g) and polyethylene glycol methyl ether methacrylate (PEGMA, 10.00 g) were dissolved in 300 g of pure water, 2-vinylpyridine (2-VP, 48.00 g) and divinylbenzene (DVB, 2.00 g) were then added thereto, and stirred at 150 rpm and 30° C. for 50 minutes and then at 60° C. for 30 minutes under a nitrogen atmosphere. After the stirring, 2,2-azobis(2-methylpropionamidine)dihydrochloride (AIBA, 0.50 g) dissolved in 18.00 g of pure water was added dropwise for 2 minutes and stirred at 150 rpm and 60° C. for 3.5 hours, and thus resin particles with an average particle size of 380 nm were obtained. An operation in which precipitation was performed by centrifugation (at 9000 rpm for 45 minutes), a supernatant was removed, and dispersion was then performed again in pure water was performed three times, and impurities were then removed by a dialysis treatment. Then, the concentration was adjusted and a 10 wt % resin particle dispersion was obtained.

245 ml of pure water was added to the resin particle dispersion (90 ml), a 400 mM chloroplatinic acid aqueous solution (90 ml) was then added thereto and the mixture was stirred at 60 rpm and 30° C. for 3 hours and then left at room temperature for 24 hours. Then, an operation in which the resin particles were precipitated by centrifugation (at 3100 rpm for 30 minutes) and a supernatant was removed was performed three times, and thus an excess chloroplatinic acid was removed. Then, the concentration was adjusted and a dispersion with 5 wt % platinum ions-attached resin particles was prepared.

Next, the dispersion with 5 wt % platinum ions-attached resin particles (55 ml) was added to 3825 ml of pure water and a 132 mM dimethylamine borane aqueous solution (110 ml) was added dropwise for 20 minutes with stirring at 160 rpm and 3° C., and then stirred at 160 rpm and 3° C. for 1 hour. Then, the mixture was stirred at 160 rpm and 25° C. for 3 hours, and thus resin-platinum composites with an average particle size of 393 nm were obtained. An operation in which the resin-platinum composites were precipitated by centrifugation (at 3100 rpm for 60 minutes), a supernatant was removed, and dispersion was then performed again in pure water was performed three times, and impurities were then removed by purification according to a dialysis treatment. Then, the concentration was adjusted and a 1 wt % resin-platinum composite dispersion was obtained. The absorbance of the produced resin-platinum composite dispersion was measured according to the above method. The result was 0.74. In addition, the average particle size of the formed platinum particles was 6 nm and the supported amount of platinum was 38.0 wt %. In the resin-platinum composite, the platinum particles included enclosed platinum particles that were completely enclosed in the resin particle, partially exposed platinum particles having a portion that was embedded in the resin particle and a portion that was exposed to the outside of the resin particle, and surface-attached platinum particles that were attached to the surface of the resin particle. At least some of the platinum particles were distributed three-dimensionally on the surface layer section of the resin particle. Here, 93 wt % of the platinum particles were in a range of 40% of the particle radius in the depth direction from the surface of the resin particle.

Using the obtained resin-platinum composite, the dispersibility when the antibody was bound was evaluated according to the following "dispersibility evaluation." As a result, all of the binding buffer solutions a, b, and c were A. Therefore, in the following evaluation by immunochromatography, binding of influenza antibodies and blocking using bovine serum albumin were performed at a pH of 8.5 (binding buffer solution c).

<Evaluation by Immunochromatography>

A resin-platinum composite-labeled antibody dispersion was produced by performing the same operation as in Example 1.

Using the produced resin-platinum composite-labeled antibody dispersion, performance of the resin-platinum composite dispersion was evaluated by performing measurement by immunochromatography. The results are shown below.

TABLE 3

| | | Slot No. | | | | | | | | | | | |
|---|---|---|---|---|---|---|---|---|---|---|---|---|---|
| | | 1 | 2 | 3 | 4 | 5 | 6 | 7 | 8 | 9 | 10 | 11 | 12 |
| Antigen dilution series | | APC × 1 | APC × 2 | APC × 4 | APC × 8 | APC × 16 | APC × 32 | APC × 64 | APC × 128 | APC × 256 | APC × 512 | APC × 1024 | Negative control |
| Color development level | After 5 minutes | 5.0 | 4.0 | 3.0 | 2.5 | 1.5 | 1.0 | 0.5 | 0.1 | 0.1 | 0 | 0 | 0 |
| | After 10 minutes | 6.0 | 5.0 | 4.0 | 3.5 | 2.5 | 2.0 | 1.0 | 0.5 | 0.5 | 0.1 | 0 | 0 |

TABLE 3-continued

| | Slot No. | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| After 15 minutes | 6.5 | 5.5 | 4.5 | 4.0 | 3.0 | 2.5 | 1.5 | 1.0 | 0.5 | 0.5 | 0.1 | 0 |

Based on the above Table 3, it was confirmed that the resin-platinum composite-labeled antibody exhibited favorable color development with respect to antigens diluted 512-fold.

Example 4

<Synthesis of Resin Particles>

ALIQUAT® 336 [made by Aldrich Co.] (1.00 g) and polyethylene glycol methyl ether methacrylate (PEGMA, 10.00 g) were dissolved in 300 g of pure water, 2-vinylpyridine (2-VP, 48.00 g) and divinylbenzene (DVB, 2.00 g) were then added thereto, and then stirred at 150 rpm and 30° C. for 50 minutes and then at 60° C. for 30 minutes under a nitrogen atmosphere. After the stirring, 2,2-azobis(2-methylpropionamidine)dihydrochloride (AIBA, 0.50 g) dissolved in 18.00 g of pure water was added dropwise for 2 minutes and stirred at 150 rpm and 60° C. for 3.5 hours, and thus resin particles with an average particle size of 420 nm were obtained. An operation in which precipitation was performed by centrifugation (at 9000 rpm for 45 minutes), a supernatant was removed, and dispersion was then performed again in pure water was performed three times, and impurities were then removed by a dialysis treatment. Then, the concentration was adjusted and a 10 wt % resin particle dispersion was obtained.

245 ml of pure water was added to the resin particle dispersion (90 ml), a 400 mM chloroplatinic acid aqueous solution (90 ml) was then added thereto and the mixture was stirred at 60 rpm and 30° C. for 3 hours and then left at room temperature for 24 hours. Then, an operation in which the resin particles were precipitated by centrifugation (at 3100 rpm for 30 minutes) and a supernatant was removed was performed three times, and thus an excess chloroplatinic acid was removed. Then, the concentration was adjusted and a dispersion with 5 wt % platinum ions-attached resin particles was prepared.

Next, the dispersion with 5 wt % platinum ions-attached resin particles (55 ml) was added to 3825 ml of pure water and a 132 mM dimethylamine borane aqueous solution (110 ml) was added dropwise for 20 minutes with stirring at 160 rpm and 3° C., and then stirred at 160 rpm and 3° C. for 1 hour. Then, the mixture was stirred at 160 rpm and 25° C. for 3 hours, and thus resin-platinum composites with an average particle size of 432 nm were obtained. An operation in which the resin-platinum composites were precipitated by centrifugation (at 3100 rpm for 60 minutes), a supernatant was removed, and dispersion was then performed again in pure water was performed three times, and impurities were then removed by purification according to a dialysis treatment. Then, the concentration was adjusted and a 1 wt % resin-platinum composite dispersion was obtained. The absorbance of the produced resin-platinum composite dispersion was measured according to the above method. The result was 0.77. In addition, the average particle size of the formed platinum particles was 5 nm, and the supported amount of platinum was 38.2 wt %. In the resin-platinum composite, the platinum particles included enclosed platinum particles that were completely enclosed in the resin particle, partially exposed platinum particles having a portion that was embedded in the resin particle and a portion that was exposed to the outside of the resin particle, and surface-attached platinum particles that were attached to the surface of the resin particle. At least some of the platinum particles were distributed three-dimensionally on the surface layer section of the resin particle. Here, 97 wt % of the platinum particles were in a range of 40% of the particle radius in the depth direction from the surface of the resin particle.

Using the obtained resin-platinum composite, the dispersibility when the antibody was bound was evaluated according to the following "dispersibility evaluation." As a result, all of the binding buffer solutions a, b, and c were A. Therefore, in the following evaluation by immunochromatography, binding of influenza antibodies and blocking using bovine serum albumin were performed at a pH of 8.5 (binding buffer solution c).

<Evaluation by Immunochromatography>

A resin-platinum composite-labeled antibody dispersion was produced by performing the same operation as in Example 1.

Using the produced resin-platinum composite-labeled antibody dispersion, performance of the resin-platinum composite dispersion was evaluated by performing measurement by immunochromatography. The results are shown below.

TABLE 4

| | | Slot No. | | | | | | | | | | | |
|---|---|---|---|---|---|---|---|---|---|---|---|---|---|
| | | 1 | 2 | 3 | 4 | 5 | 6 | 7 | 8 | 9 | 10 | 11 | 12 |
| Antigen dilution series | | APC × 1 | APC × 2 | APC × 4 | APC × 8 | APC × 16 | APC × 32 | APC × 64 | APC × 128 | APC × 256 | APC × 512 | APC × 1024 | Negative control |
| Color development level | After 5 minutes | 6.0 | 5.0 | 4.0 | 3.0 | 2.5 | 1.5 | 1.0 | 0.5 | 0.5 | 0.1 | 0.1 | 0 |
| | After 10 minutes | 7.0 | 6.0 | 5.0 | 4.0 | 3.5 | 2.5 | 2.0 | 1.0 | 0.5 | 0.5 | 0.1 | 0 |
| | After 15 minutes | 7.5 | 6.5 | 5.5 | 4.5 | 3.5 | 3.0 | 2.0 | 1.5 | 1.0 | 0.5 | 0.5 | 0.1 |

Based on the above Table 4, it was confirmed that the resin-platinum composite-labeled antibody exhibited favorable color development with respect to antigens diluted 1024-fold.

Example 5

<Synthesis of Resin Particles>

ALIQUAT® 336 [made by Aldrich Co.] (5.00 g) and polyethylene glycol methyl ether methacrylate (PEGMA, 10.00 g) were dissolved in 389.5 g of pure water, 2-vinylpyridine (2-VP, 48.00 g) and divinylbenzene (DVB, 2.00 g) were then added thereto, and stirred at 150 rpm and 30° C. for 50 minutes and then at 60° C. for 30 minutes under a nitrogen atmosphere. After the stirring, 2,2-azobis(2-methylpropionamidine)dihydrochloride (AIBA, 0.50 g) dissolved in 50.00 g of pure water was added dropwise for 2 minutes, and stirred at 150 rpm and 60° C. for 3.5 hours, and thus resin particles with an average particle size of 200 nm were obtained. An operation in which precipitation was performed by centrifugation (at 9000 rpm for 45 minutes), a supernatant was removed, and dispersion was then performed again in pure water was performed three times, and impurities were then removed by a dialysis treatment. Then, the concentration was adjusted and a 10 wt % resin particle dispersion was obtained.

245 ml of pure water was added to the resin particle dispersion (90 ml), a 400 mM chloroplatinic acid aqueous solution (90 ml) was then added thereto and the mixture was stirred at 60 rpm and 30° C. for 3 hours and then left at room temperature for 24 hours. Then, an operation in which the resin particles were precipitated by centrifugation (at 3100 rpm for 30 minutes) and a supernatant was removed was performed three times, and thus an excess chloroplatinic acid was removed. Then, the concentration was adjusted and a dispersion with 5 wt % platinum ions-attached resin particles was prepared.

Next, the dispersion with 5 wt % platinum ions-attached resin particles (55 ml) was added to 3825 ml of pure water and a 132 mM dimethylamine borane aqueous solution (110 ml) was added dropwise for 20 minutes with stirring at 160 rpm and 3° C., and then stirred at 160 rpm and 3° C. for 1 hour. Then, the mixture was stirred at 160 rpm and 25° C. for 3 hours and thus resin-platinum composites with an average particle size of 215 nm were obtained. An operation in which the resin-platinum composites were precipitated by centrifugation (at 3100 rpm for 60 minutes), a supernatant was removed, and dispersion was then performed again in pure water was performed three times, and impurities were then removed by purification according to a dialysis treatment. Then, the concentration was adjusted and a 1 wt % resin-platinum composite dispersion was obtained. The absorbance of the produced resin-platinum composite dispersion was measured according to the above method. The result was 0.57. In addition, the average particle size of the formed platinum particles was 6 nm and the supported amount of platinum was 37.1 wt %. In the resin-platinum composite, the platinum particles included enclosed platinum particles that were completely enclosed in the resin particle, partially exposed platinum particles having a portion that was embedded in the resin particle and a portion that was exposed to the outside of the resin particle, and surface-attached platinum particles that were attached to the surface of the resin particle. At least some of the platinum particles were distributed three-dimensionally on the surface layer section of the resin particle. Here, 83 wt % of the platinum particles were in a range of 40% of the particle radius in the depth direction from the surface of the resin particle.

Using the obtained resin-platinum composite, the dispersibility when the antibody was bound was evaluated according to the following "dispersibility evaluation." As a result, all of the binding buffer solutions a, b, and c were A. Therefore, in the following evaluation by immunochromatography, binding of influenza antibodies and blocking using bovine serum albumin were performed at a pH of 8.5 (binding buffer solution c).

<Evaluation by Immunochromatography>

A resin-platinum composite-labeled antibody dispersion was produced by performing the same operation as in Example 1.

Using the produced resin-platinum composite-labeled antibody dispersion, performance of the resin-platinum composite dispersion was evaluated by performing measurement by immunochromatography. The results are shown below.

TABLE 5

| | | Slot No. | | | | | | | | | | | |
|---|---|---|---|---|---|---|---|---|---|---|---|---|---|
| | | 1 | 2 | 3 | 4 | 5 | 6 | 7 | 8 | 9 | 10 | 11 | 12 |
| Antigen dilution series | | APC × 1 | APC × 2 | APC × 4 | APC × 8 | APC × 16 | APC × 32 | APC × 64 | APC × 128 | APC × 256 | APC × 512 | APC × 1024 | Negative control |
| Color development level | After 5 minutes | 4.0 | 3.5 | 3.0 | 2.0 | 1.0 | 0.5 | 0.1 | 0 | 0 | 0 | 0 | 0 |
| | After 10 minutes | 5.0 | 4.5 | 3.5 | 2.5 | 1.5 | 1.0 | 0.5 | 0.1 | 0.1 | 0 | 0 | 0 |
| | After 15 minutes | 5.5 | 5.0 | 4.0 | 3.0 | 2.0 | 1.5 | 1.0 | 0.5 | 0.1 | 0 | 0 | 0 |

Based on the above Table 5, it was confirmed that the resin-platinum composite-labeled antibody exhibited favorable color development with respect to antigens diluted 128-fold.

Example 6

<Synthesis of Resin Particles>

ALIQUAT® 336 [made by Aldrich Co.] (2.50 g) and polyethylene glycol methyl ether methacrylate (PEGMA, 5.00 g) were dissolved in 400 g of pure water, 2-vinylpyridine (2-VP, 24.75 g) and divinylbenzene (DVB, 0.25 g) were then added thereto, and stirred at 150 rpm and 30° C. for 50 minutes and then at 60° C. for 30 minutes under a nitrogen atmosphere. After the stirring, 2,2-azobis(2-methylpropionamidine)dihydrochloride (AIBA, 0.25 g) dissolved in 22.00 g of pure water was added dropwise for 2 minutes, and stirred at 150 rpm and 60° C. for 3.5 hours, and thus resin particles with an average particle size of 140 nm were obtained. An operation in which precipitation was performed by centrifugation (at 9000 rpm for 45 minutes), a supernatant was removed, and dispersion was then performed again in pure water was performed three times, and impurities were then removed by a dialysis treatment. Then, the concentration was adjusted and a 10 wt % resin particle dispersion was obtained.

245 ml of pure water was added to the resin particle dispersion (90 ml), a 400 mM chloroplatinic acid aqueous solution (90 ml) was then added thereto and the mixture was stirred at 60 rpm and 30° C. for 3 hours and then left at room temperature for 24 hours. Then, an operation in which the resin particles were precipitated by centrifugation (at 3100 rpm for 30 minutes) and a supernatant was removed was performed three times, and thus an excess chloroplatinic acid was removed. Then, the concentration was adjusted and a dispersion with 5 wt % platinum ions-attached resin particles was prepared.

Next, the dispersion with 5 wt % platinum ions-attached resin particles (55 ml) was added to 3825 ml of pure water and a 132 mM dimethylamine borane aqueous solution (110 ml) was added dropwise for 20 minutes with stirring at 160 rpm and 3° C., and then stirred at 160 rpm and 3° C. for 1 hour. Then, the mixture was stirred at 160 rpm and 25° C. for 3 hours, and thus resin-platinum composites with an average particle size of 154 nm were obtained. An operation in which the resin-platinum composites were precipitated by centrifugation (at 3100 rpm for 60 minutes), a supernatant was removed, and dispersion was then performed again in pure water was performed three times, and impurities were then removed by purification according to a dialysis treatment. Then, the concentration was adjusted and a 1 wt % resin-platinum composite dispersion was obtained. The absorbance of the produced resin-platinum composite dispersion was measured according to the above method. The result was 0.48. In addition, the average particle size of the formed platinum particles was 3 nm, and the supported amount of platinum was 34.5 wt %. In the resin-platinum composite, the platinum particles included enclosed platinum particles that were completely enclosed in the resin particle, partially exposed platinum particles having a portion that was embedded in the resin particle and a portion that was exposed to the outside of the resin particle, and surface-attached platinum particles that were attached to the surface of the resin particle. At least some of the platinum particles were distributed three-dimensionally on the surface layer section of the resin particle.

Using the obtained resin-platinum composite, the dispersibility when the antibody was bound was evaluated according to the following "dispersibility evaluation." As a result, all of the binding buffer solutions a, b, and c were A.

Therefore, in the following evaluation by immunochromatography, binding of influenza antibodies and blocking using bovine serum albumin were performed at a pH of 8.5 (binding buffer solution c).

<Evaluation by Immunochromatography>

A resin-platinum composite-labeled antibody dispersion was produced by performing the same operation as in Example 1.

Using the produced resin-platinum composite-labeled antibody dispersion, performance of the resin-platinum composite dispersion was evaluated by performing measurement by immuno chromatography. The results are shown below.

TABLE 6

| | | Slot No. | | | | | | | | | | | |
|---|---|---|---|---|---|---|---|---|---|---|---|---|---|
| | | 1 | 2 | 3 | 4 | 5 | 6 | 7 | 8 | 9 | 10 | 11 | 12 |
| Antigen dilution series | | APC × 1 | APC × 2 | APC × 4 | APC × 8 | APC × 16 | APC × 32 | APC × 64 | APC × 128 | APC × 256 | APC × 512 | APC × 1024 | Negative control |
| Color development level | After 5 minutes | 4.5 | 3.5 | 2.5 | 2.0 | 1.5 | 0.5 | 0.1 | 0 | 0 | 0 | 0 | 0 |
| | After 10 minutes | 5.0 | 4.0 | 3.5 | 2.5 | 2.0 | 1.0 | 0.5 | 0.1 | 0 | 0 | 0 | 0 |
| | After 15 minutes | 5.5 | 4.5 | 4.0 | 2.5 | 2.0 | 1.0 | 0.5 | 0.1 | 0.1 | 0 | 0 | 0 |

Based on the above Table 6, it was confirmed that the resin-platinum composite-labeled antibody exhibited favorable color development with respect to antigens diluted 64-fold.

Example 7

<Synthesis of Resin Particles>

ALIQUAT® 336 [made by Aldrich Co.] (0.25 g) and polyethylene glycol methyl ether methacrylate (PEGMA, 5.00 g) were dissolved in 325 g of pure water, 2-vinylpyridine (2-VP, 24.75 g) and divinylbenzene (DVB, 0.25 g) were then added thereto and stirred at 150 rpm and 30° C. for 50 minutes and then at 60° C. for 30 minutes under a nitrogen atmosphere. After the stirring, 2,2-azobis(2-methylpropionamidine)dihydrochloride (AIBA, 0.25 g) dissolved in 18.00 g of pure water was added dropwise for 2 minutes and stirred at 150 rpm and 60° C. for 3.5 hours, and thus resin particles with an average particle size of 260 nm were obtained. An operation in which precipitation was performed by centrifugation (at 9000 rpm for 45 minutes), a supernatant was removed, and dispersion was then performed again in pure water was performed three times, and impurities were then removed by a dialysis treatment. Then, the concentration was adjusted and a 10 wt % resin particle dispersion was obtained.

245 ml of pure water was added to the resin particle dispersion (90 ml), a 400 mM chloroplatinic acid aqueous solution (90 ml) was then added thereto and the mixture was stirred at 60 rpm and 30° C. for 3 hours and then left at room temperature for 24 hours. Then, an operation in which the resin particles were precipitated by centrifugation (at 3100 rpm for 30 minutes) and a supernatant was removed was performed three times, and thus an excess chloroplatinic acid was removed. Then, the concentration was adjusted and a dispersion with 5 wt % platinum ions-attached resin particles was prepared.

Next, the dispersion with 5 wt % platinum ions-attached resin particles (55 ml) was added to 3825 ml of pure water and a 132 mM dimethylamine borane aqueous solution (110 ml) was added dropwise for 20 minutes with stirring at 160 rpm and 3° C., and then stirred at 160 rpm and 3° C. for 1 hour. Then, the mixture was stirred at 160 rpm and 25° C. for 3 hours and thus resin-platinum composites with an average particle size of 265 nm were obtained. An operation in which the resin-platinum composites were precipitated by centrifugation (at 3100 rpm for 60 minutes), a supernatant was removed, and dispersion was then performed again in pure water was performed three times, and impurities were then removed by purification according to a dialysis treatment. Then, the concentration was adjusted and a 1 wt % resin-platinum composite dispersion was obtained. The absorbance of the produced resin-platinum composite dispersion was measured according to the above method. The result was 0.83. In addition, the average particle size of the formed platinum particles was 3 nm, and the supported amount of platinum was 35.8 wt %. In the resin-platinum composite, the platinum particles included enclosed platinum particles that were completely enclosed in the resin particle, partially exposed platinum particles having a portion that was embedded in the resin particle and a portion that was exposed to the outside of the resin particle, and surface-attached platinum particles that were attached to the surface of the resin particle. At least some of the platinum particles were distributed three-dimensionally on the surface layer section of the resin particle.

Using the obtained resin-platinum composite, the dispersibility when the antibody was bound was evaluated according to the following "dispersibility evaluation." As a result, all of the binding buffer solutions a, b, and c were A. Therefore, in the following evaluation by immunochromatography, binding of influenza antibodies and blocking using bovine serum albumin were performed at a pH of 8.5 (binding buffer solution c).

<Evaluation by Immunochromatography>

A resin-platinum composite-labeled antibody dispersion was produced by performing the same operation as in Example 1.

Using the produced resin-platinum composite-labeled antibody dispersion, performance of the resin-platinum composite dispersion was evaluated by performing measurement by immunochromatography. The results are shown below.

dine (2-VP, 49.50 g) and divinylbenzene (DVB, 0.50 g) were then added thereto and stirred at 150 rpm and 30° C. for 50 minutes and then at 60° C. for 30 minutes under a nitrogen atmosphere. After the stirring, 2,2-azobis(2-methylpropionamidine)dihydrochloride (AIBA, 0.50 g) dissolved in 18.00 g of pure water was added dropwise for 1 minute and stirred at 150 rpm and 60° C. for 3.5 hours, and thus resin particles with an average particle size of 512 nm were obtained. An operation in which precipitation was performed by centrifugation (at 9000 rpm for 45 minutes), a supernatant was removed, and dispersion was then performed again in pure water was performed three times, and impurities were then removed by a dialysis treatment. Then, the concentration was adjusted and a 10 wt % resin particle dispersion was obtained.

245 ml of pure water was added to the resin particle dispersion (90 ml), a 400 mM chloroplatinic acid aqueous solution (90 ml) was then added thereto and the mixture was stirred at 60 rpm and 30° C. for 3 hours and then left at room temperature for 24 hours. Then, an operation in which the resin particles were precipitated by centrifugation (at 3100 rpm for 30 minutes) and a supernatant was removed was performed three times, and thus an excess chloroplatinic acid was removed. Then, the concentration was adjusted and a dispersion with 5 wt % platinum ions-attached resin particles was prepared.

Next, the dispersion with 5 wt % platinum ions-attached resin particles (55 ml) was added to 3825 ml of pure water and a 132 mM dimethylamine borane aqueous solution (110 ml) was added dropwise for 20 minutes with stirring at 160 rpm and 3° C., and then stirred at 160 rpm and 3° C. for 1 hour. Then, the mixture was stirred at 160 rpm and 25° C. for 3 hours and thus resin-platinum composites with an average particle size of 537 nm were obtained. An operation in which the resin-platinum composites were precipitated by centrifugation (at 3100 rpm for 60 minutes), a supernatant was removed, and dispersion was then performed again in pure water was performed three times, and impurities were then removed by purification according to a dialysis treatment. Then, the concentration was adjusted and a 1 wt % resin-platinum composite dispersion was obtained. The

TABLE 7

| | | Slot No. | | | | | | | | | | | |
|---|---|---|---|---|---|---|---|---|---|---|---|---|---|
| | | 1 | 2 | 3 | 4 | 5 | 6 | 7 | 8 | 9 | 10 | 11 | 12 |
| Antigen dilution series | | APC × 1 | APC × 2 | APC × 4 | APC × 8 | APC × 16 | APC × 32 | APC × 64 | APC × 128 | APC × 256 | APC × 512 | APC × 1024 | Negative control |
| Color development level | After 5 minutes | 5.0 | 4.0 | 3.0 | 2.5 | 1.5 | 1.0 | 0.5 | 0 | 0 | 0 | 0 | 0 |
| | After 10 minutes | 6.0 | 5.0 | 4.0 | 3.5 | 2.0 | 1.5 | 0.5 | 0.1 | 0 | 0 | 0 | 0 |
| | After 15 minutes | 6.0 | 5.0 | 4.0 | 3.5 | 2.0 | 1.5 | 1.0 | 0.5 | 0.1 | 0 | 0 | 0 |

Based on the above Table 7, it was confirmed that the resin-platinum composite-labeled antibody exhibited favorable color development with respect to antigens diluted 128-fold.

Example 8

<Synthesis of Resin Particles>

ALIQUAT® 336 [made by Aldrich Co.] (0.50 g) and polyethylene glycol methyl ether methacrylate (PEGMA, 10.00 g) were dissolved in 300 g of pure water, 2-vinylpyriabsorbance of the produced resin-platinum composite dispersion was measured according to the above method. The result was 0.75. In addition, the average particle size of the formed platinum particles was 6 nm, and the supported amount of platinum was 39.0 wt %. In the resin-platinum composite, the platinum particles included enclosed platinum particles that were completely enclosed in the resin particle, partially exposed platinum particles having a portion that was embedded in the resin particle and a portion that was exposed to the outside of the resin particle, and surface-attached platinum particles that were attached to the surface of the resin particle. At least some of the platinum particles were distributed three-dimensionally on the surface layer section of the resin particle.

Using the obtained resin-platinum composite, the dispersibility when the antibody was bound was evaluated according to the following "dispersibility evaluation." As a result, all of the binding buffer solutions a, b, and c were A. Therefore, in the following evaluation by immunochromatography, binding of influenza antibodies and blocking using bovine serum albumin were performed at a pH of 8.5 (binding buffer solution c).

<Evaluation by Immunochromatography>

A resin-platinum composite-labeled antibody dispersion was produced by performing the same operation as in Example 1.

Using the produced resin-platinum composite-labeled antibody dispersion, performance of the resin-platinum composite dispersion was evaluated by performing measurement by immunochromatography. The results are shown below.

TABLE 8

| | | Slot No. | | | | | | | | | | | |
|---|---|---|---|---|---|---|---|---|---|---|---|---|---|
| | | 1 | 2 | 3 | 4 | 5 | 6 | 7 | 8 | 9 | 10 | 11 | 12 |
| Antigen dilution series | | APC × 1 | APC × 2 | APC × 4 | APC × 8 | APC × 16 | APC × 32 | APC × 64 | APC × 128 | APC × 256 | APC × 512 | APC × 1024 | Negative control |
| Color development level | After 5 minutes | 6.0 | 5.0 | 4.5 | 3.5 | 2.5 | 1.5 | 1.0 | 0.5 | 0.5 | 0.1 | 0.1 | 0 |
| | After 10 minutes | 7.0 | 6.0 | 5.0 | 4.0 | 3.5 | 2.5 | 2.0 | 1.0 | 1.0 | 0.5 | 0.5 | 0 |
| | After 15 minutes | 7.5 | 6.5 | 5.5 | 4.5 | 3.5 | 3.0 | 2.0 | 1.5 | 1.0 | 0.5 | 0.5 | 0.1 |

Based on the above Table 8, it was confirmed that the resin-platinum composite-labeled antibody exhibited favorable color development with respect to antigens diluted 1024-fold.

Example 9

<Synthesis of Resin Particles>

ALIQUAT® 336 [made by Aldrich Co.] (1.00 g) and polyethylene glycol methyl ether methacrylate (PEGMA, 10.00 g) were dissolved in 300 g of pure water, 2-vinylpyridine (2-VP, 48.00 g) and divinylbenzene (DVB, 2.00 g) were then added thereto, and then stirred at 150 rpm and 30° C. for 50 minutes and then at 60° C. for 30 minutes under a nitrogen atmosphere. After the stirring, 2,2-azobis(2-methylpropionamidine)dihydrochloride (AIBA, 0.50 g) dissolved in 18.00 g of pure water was added dropwise for 2 minutes and stirred at 150 rpm and 60° C. for 3.5 hours, and thus resin particles with an average particle size of 420 run were obtained. An operation in which precipitation was performed by centrifugation (at 9000 rpm for 45 minutes), a supernatant was removed, and dispersion was then performed again in pure water was performed three times, and impurities were then removed by a dialysis treatment. Then, the concentration was adjusted and a 10 wt % resin particle dispersion was obtained.

245 ml of pure water was added to the resin particle dispersion (90 ml), a 400 mM chloroplatinic acid aqueous solution (90 ml) was then added thereto and the mixture was stirred at 60 rpm and 30° C. for 3 hours and then left at room temperature for 24 hours. Then, an operation in which the resin particles were precipitated by centrifugation (at 3100 rpm for 30 minutes) and a supernatant was removed was performed three times, and thus an excess chloroplatinic acid was removed. Then, the concentration was adjusted and a dispersion with 5 wt % platinum ions-attached resin particles was prepared.

Next, the dispersion with 5 wt % platinum ions-attached resin particles (55 ml) was added to 3825 ml of pure water and a 132 mM dimethylamine borane aqueous solution (110 ml) was added dropwise for 120 minutes with stirring at 160 rpm and 3° C., and then stirred at 160 rpm and 3° C. for 1 hour. Then, the mixture was stirred at 160 rpm and 25° C. for 3 hours and thus resin-platinum composites with an average particle size of 432 nm were obtained. An operation in which the resin-platinum composites were precipitated by centrifugation (at 3100 rpm for 60 minutes), a supernatant was removed, and dispersion was then performed again in pure water was performed three times, and impurities were then removed by purification according to a dialysis treatment. Then, the concentration was adjusted and a 1 wt % resin-platinum composite dispersion was obtained. The absorbance of the produced resin-platinum composite dispersion was measured according to the above method. The result was 0.72. In addition, the average particle size of the formed platinum particles was 28 nm, and the supported amount of platinum was 38.2 wt %. In the resin-platinum composite, the platinum particles included enclosed platinum particles that were completely enclosed in the resin particle, partially exposed platinum particles having a portion that was embedded in the resin particle and a portion that was exposed to the outside of the resin particle, and surface-attached platinum particles that were attached to the surface of the resin particle. At least some of the platinum particles were distributed three-dimensionally on the surface layer section of the resin particle.

Using the obtained resin-platinum composite, the dispersibility when the antibody was bound was evaluated according to the following "dispersibility evaluation." As a result, all of the binding buffer solutions a, b, and c were A. Therefore, in the following evaluation by immunochromatography, binding of influenza antibodies and blocking using bovine serum albumin were performed at a pH of 8.5 (binding buffer solution c).

<Evaluation by Immunochromatography>

A resin-platinum composite-labeled antibody dispersion was produced by performing the same operation as in Example 1.

Using the produced resin-platinum composite-labeled antibody dispersion, performance of the resin-platinum composite dispersion was evaluated by performing measurement by immunochromatography. The results are shown below.

TABLE 9

| | | \multicolumn{12}{c}{Slot No.} |
| | | 1 | 2 | 3 | 4 | 5 | 6 | 7 | 8 | 9 | 10 | 11 | 12 |
|---|---|---|---|---|---|---|---|---|---|---|---|---|---|
| Antigen dilution series | | APC × 1 | APC × 2 | APC × 4 | APC × 8 | APC × 16 | APC × 32 | APC × 64 | APC × 128 | APC × 256 | APC × 512 | APC × 1024 | Negative control |
| Color development level | After 5 minutes | 5.0 | 4.0 | 3.0 | 2.5 | 1.5 | 1.0 | 0.5 | 0.1 | 0.1 | 0 | 0 | 0 |
| | After 10 minutes | 6.0 | 5.0 | 4.0 | 3.5 | 2.5 | 2.0 | 1.0 | 0.5 | 0.5 | 0.1 | 0 | 0 |
| | After 15 minutes | 6.5 | 5.5 | 4.5 | 4.0 | 3.0 | 2.5 | 1.5 | 1.0 | 0.5 | 0.5 | 0.1 | 0 |

Based on the above Table 9, it was confirmed that the resin-platinum composite-labeled antibody exhibited favorable color development with respect to antigens diluted 512-fold.

Comparative Example 1

<Evaluation by Immunochromatography>

100 μg of influenza antibodies were mixed into 1 ml (0.1 wt %) of colored latex (made by Merck Millipore, color Estapor functional particles, K1030, average particle size: 392 nm, the absorbance at 570 nm; 0.83, and the absorbance at 700 nm; 0.36), and stirred at room temperature for about 3 hours, and the antibodies were bound to the colored latex. A bovine serum albumin solution was added so that the final concentration was 1% and stirred at room temperature for 2 hours, and the colored latex was blocked. Centrifugation was performed at 12000 rpm and 4° C. for 5 minutes for recovery, suspending in a buffer solution including 0.2% bovine serum albumin was performed, and colored latex-labeled antibodies were produced.

Using the produced colored latex-labeled antibodies, measurement was performed according to the following immunochromatography, and the performance of the colored latex was evaluated.

(Evaluation Method)

A monochrome screen for influenza type A evaluation (made by Adtec Co.) was used for evaluation. Color development levels after 5 minutes, after 10 minutes, and after 15 minutes were compared. In performance evaluation, for antigens, two-fold serial dilutions (1-fold to 1024-fold) of an influenza type A positive control (APC) were used (the concentration of virus before APC dilution was 5000 FFU/ml).

(Evaluation Procedure)

3 μL of the colored latex-labeled antibodies were put into each well of a 96-well plate, and 100 μL of two-fold serial dilutions (1-fold to 1024-fold) of the APC and 100 μL of a negative control were mixed. Next, 50 μL of the result was added to a monochrome screen for influenza type A evaluation, and color development levels were evaluated after 5 minutes, after 10 minutes, and after 15 minutes. The color development level was determined using a color sample for gold colloid determination (made by Adtec Co.). The results are shown below.

TABLE 10

| | | \multicolumn{12}{c}{Slot No.} |
| | | 1 | 2 | 3 | 4 | 5 | 6 | 7 | 8 | 9 | 10 | 11 | 12 |
|---|---|---|---|---|---|---|---|---|---|---|---|---|---|
| | | \multicolumn{12}{c}{Colored latex} |
| Antigen dilution series | | APC × 1 | APC × 2 | APC × 4 | APC × 8 | APC × 16 | APC × 32 | APC × 64 | APC × 128 | APC × 256 | APC × 512 | APC × 1024 | Negative control |
| Color development level | After 5 minutes | 3.5 | 2.0 | 1.0 | 0.5 | 0.1 | 0 | 0 | 0 | 0 | 0 | 0 | 0 |
| | After 10 minutes | 4.0 | 2.5 | 1.5 | 0.5 | 0.1 | 0.1 | 0 | 0 | 0 | 0 | 0 | 0 |
| | After 15 minutes | 4.5 | 3.5 | 2.5 | 1.0 | 0.5 | 0.1 | 0.1 | 0 | 0 | 0 | 0 | 0 |

Based on the above Table 10, it was confirmed that the colored latex-labeled antibody exhibited favorable color development with respect to antigens diluted 16-fold.

The measurement results of the absorbance at 700 nm in the above Examples 1 to 9 and Comparative Example 1 are summarized in Table 11 and Table 12.

TABLE 11

|  | Example 1 | Example 2 | Example 3 | Example 4 | Example 5 | Example 6 | Example 7 |
|---|---|---|---|---|---|---|---|
| Absorbance at 700 nm | 0.70 | 0.70 | 0.74 | 0.77 | 0.57 | 0.48 | 0.83 |
| Evaluation | A | A | A | A | B | B | A |

TABLE 12

|  | Example 8 | Example 9 | Comparative Example 1 |
|---|---|---|---|
| Absorbance at 700 nm | 0.75 | 0.72 | 0.36 |
| Evaluation | A | A | C |

Comparative Example 2

<Synthesis of Gold Colloids>

250 ml of a 1 mM chloroauric acid aqueous solution was put into a 500 ml three-neck round bottom flask. The mixture was stirred strongly and boiled using a heating and refluxing device. After the boiling, 25 ml of a 38.8 mM sodium citrate aqueous solution was added thereto, and it was confirmed that the solution changed from a light yellow to a dark red. Heating was continued for 10 minutes with stirring, and the mixture was then stirred and cooled at room temperature for about 30 minutes. The solution was filtered using a membrane filter with a pore size of 2 μm, and transferred to an Erlenmeyer flask and stored in a cool and dark place. The average particle size of the produced gold colloids was 12.3 nm. In addition, the absorbance was measured according to the above method, and the result was 1.32.

<Evaluation by Immunochromatography>

100 μg of influenza antibodies were mixed into 1 ml (OD=10) of the obtained gold colloids, the mixture was stirred at room temperature for about 3 hours, and antibodies were bound to gold colloids. A bovine serum albumin solution was added so that the final concentration was 1%, and stirred at room temperature for 2 hours, and the surface of the gold colloids was blocked. Centrifugation was performed at 12000 rpm and 4° C. for 5 minutes for recovery, suspending in a buffer solution including 0.2% bovine serum albumin was performed, and gold colloid-labeled antibodies were produced.

Using the produced gold colloid-labeled antibodies, measurement was performed according to the following immunochromatography, and the performance of the gold colloids was evaluated.

(Evaluation Method)

The evaluation was performed in the same manner as in Comparative Example 1.

(Evaluation Procedure)

3 μL of the gold colloid-labeled antibodies were put into each well of a 96-well plate, and 100 μL of two-fold serial dilutions (1-fold to 1024-fold) of the APC and 100 μL of a negative control were mixed. Next, 50 μL of the result was added to a monochrome screen for influenza type A evaluation, and color development levels were evaluated after 5 minutes, after 10 minutes, and after 15 minutes. The color development level was determined using a color sample for gold colloid determination (made by Adtec Co.). The results are shown below.

TABLE 13

| | | Slot No. | | | | | | | | | | | |
|---|---|---|---|---|---|---|---|---|---|---|---|---|---|
| | | 1 | 2 | 3 | 4 | 5 | 6 | 7 | 8 | 9 | 10 | 11 | 12 |
| | | Gold colloid | | | | | | | | | | | |
| Antigen dilution series | | APC × 1 | APC × 2 | APC × 4 | APC × 8 | APC × 16 | APC × 32 | APC × 64 | APC × 128 | APC × 256 | APC × 512 | APC × 1024 | Negative control |
| Color development level | After 5 minutes | 4.0 | 3.0 | 2.0 | 1.5 | 0.5 | 0.1 | 0 | 0 | 0 | 0 | 0 | 0 |
| | After 10 minutes | 4.5 | 3.5 | 2.5 | 2.0 | 1.0 | 0.5 | 0.1 | 0 | 0 | 0 | 0 | 0 |
| | After 15 minutes | 5.0 | 4.5 | 3.5 | 3.0 | 2.0 | 1.0 | 0.1 | 0.1 | 0 | 0 | 0 | 0 |

Based on the above Table 13, it was confirmed that the gold colloid-labeled antibody exhibited favorable color development with respect to antigens diluted 32-fold.

Comparative Example 3

<Synthesis of Resin Particles>

ALIQUAT® 336 [made by Aldrich Co.] (1.00 g) and polyethylene glycol methyl ether methacrylate (PEGMA, 10.00 g) were dissolved in 300 g of pure water, 2-vinylpyridine (2-VP, 48.00 g) and divinylbenzene (DVB, 2.00 g) were then added thereto, and then stirred at 150 rpm and 30° C. for 50 minutes and then at 60° C. for 30 minutes under a nitrogen atmosphere. After the stirring, 2,2-azobis(2-methylpropionamidine)dihydrochloride (AIBA, 0.500 g) dissolved in 18.00 g of pure water was added dropwise for 2 minutes and stirred at 150 rpm and 60° C. for 3.5 hours, and thus resin particles with an average particle size of 420 nm were obtained. An operation in which precipitation was performed by centrifugation (at 9000 rpm for 60 minutes), a supernatant was removed, and dispersion was then performed again in pure water was performed three times, and impurities were then removed by a dialysis treatment. Then, the concentration was adjusted and a 10 wt % resin particle dispersion was obtained.

1233 ml of pure water was added to the above resin particle dispersion (50 ml), and a 30 mM chloroauric acid aqueous solution (100 ml) was then added thereto, and the mixture was left at room temperature for 24 hours. Then, an operation in which resin particles were precipitated by centrifugation (at 3100 rpm for 30 minutes) and a supernatant was removed was performed three times, and thus an excess chloroauric acid was removed. Then, the concentration was adjusted and a 2.5 wt % gold-ion-attached resin particle dispersion was prepared.

Next, the 2.5 wt % gold-ion-attached resin particle dispersion (42.4 ml) was added to 1580 ml of pure water, a 528 mM dimethylamine borane aqueous solution (10 ml) was stirred at room temperature for about 3 hours, and the antibody was bound to the resin-gold composite. A bovine serum albumin solution was added so that the final concentration was 1% and stirred at room temperature for 2 hours, and the surface of the resin-gold composite was blocked. Centrifugation was performed at 12000 rpm and 4° C. for 5 minutes for recovery, suspending in a buffer solution including 0.2% bovine serum albumin was performed, and a resin-gold composite-labeled antibody dispersion was produced.

Using the produced resin-gold composite-labeled antibody dispersion, measurement was performed according to the following immunochromatography, and the performance of the resin-gold composite dispersion was evaluated. The results are shown below.

TABLE 14

| | | Slot No. | | | | | | | | | | | |
|---|---|---|---|---|---|---|---|---|---|---|---|---|---|
| | | 1 | 2 | 3 | 4 | 5 | 6 | 7 | 8 | 9 | 10 | 11 | 12 |
| Antigen dilution series | | APC × 1 | APC × 2 | APC × 4 | APC × 8 | APC × 16 | APC × 32 | APC × 64 | APC × 128 | APC × 256 | APC × 512 | APC × 1024 | Negative control |
| Color development level | After 5 minutes | 4.5 | 4.0 | 3.5 | 3.0 | 2.0 | 1.5 | 0.5 | 0.5 | 0.1 | 0 | 0 | 0 |
| | After 10 minutes | 5.5 | 5.0 | 4.5 | 3.5 | 3.0 | 2.0 | 1.5 | 0.5 | 0.5 | 0.1 | 0 | 0 |
| | After 15 minutes | 6.5 | 6.0 | 5.0 | 4.5 | 3.5 | 2.5 | 2.0 | 1.0 | 0.5 | 0.1 | 0 | 0 | added dropwise for 2 minutes with stirring at 160 rpm and 20° C., and then the mixture was stirred at room temperature for 2 hours, and thus resin-gold composites with an average particle size of 438 nm were obtained. An operation in which the resin-gold composites were precipitated by centrifugation (at 3100 rpm for 60 minutes), a supernatant was removed, and dispersion was then performed again in pure water was performed three times, and purification was then performed according to a dialysis treatment. Then the concentration was adjusted and a 1 wt % resin-gold composite dispersion was obtained. The absorbance of the produced resin-gold composite was measured according to the above method. The result was 0.98. In addition, the average particle size of the formed gold particles was 25.0 nm, and the gold supported amount was 54.7 wt %. In the resin-gold composite, the gold particles included enclosed gold particles that were completely enclosed in the resin particle, partially exposed gold particles having a portion that was embedded in the resin particle and a portion that was exposed to the outside of the resin particle, and surface-attached gold particles that were attached to the surface of the resin particle. At least some of the gold particles were distributed three-dimensionally on the surface layer section of the resin particle.

Using the obtained resin-gold composite, the dispersibility when the antibody was bound was evaluated according to the following "dispersibility evaluation." As a result, both the binding buffer solutions a and b were A, but the binding buffer solution c was C. Therefore, in the following evaluation by immunochromatography, binding of influenza antibodies and blocking using bovine serum albumin were performed at a pH of 3.0 (binding buffer solution a).

<Evaluation by Immunochromatography>

100 μg of influenza antibodies were mixed into 1 ml of the obtained resin-gold composite dispersion (0.1 wt %), and Based on the Table 14, it was confirmed that the resin-gold composite-labeled antibody exhibited favorable color development with respect to antigens diluted 256-fold.

Comparative Example 4

<Synthesis of Resin Particles>

ALIQUAT® 336 [made by Aldrich Co.] (2.00 g) and polyethylene glycol methyl ether methacrylate (PEGMA, 10.00 g) were dissolved in 300 g of pure water, 2-vinylpyridine (2-VP, 48.00 g) and divinylbenzene (DVB, 2.00 g) were then added thereto, and stirred at 150 rpm and 30° C. for 50 minutes and then at 60° C. for 30 minutes under a nitrogen atmosphere. After the stirring, 2,2-azobis(2-methylpropionamidine)dihydrochloride (AIBA, 0.500 g) dissolved in 18.00 g of pure water was added dropwise for 2 minutes and stirred at 150 rpm and 60° C. for 3.5 hours, and thus resin particles with an average particle size of 380 nm were obtained. An operation in which precipitation was performed by centrifugation (at 9000 rpm for 60 minutes), a supernatant was removed, and dispersion was then performed again in pure water was performed three times, and impurities were then removed by a dialysis treatment. Then, the concentration was adjusted and a 10 wt % resin particle dispersion was obtained.

1233 ml of pure water was added to the above resin particle dispersion (50 ml), and a 30 mM chloroauric acid aqueous solution (100 ml) was then added thereto, and the mixture was left at room temperature for 24 hours. Then, an operation in which resin particles were precipitated by centrifugation (at 3100 rpm for 30 minutes) and a supernatant was removed was performed three times, and thus an excess chloroauric acid was removed. Then, the concentration was adjusted and a 2.5 wt % gold-ion-attached resin particle dispersion was prepared.

Next, the 2.5 wt % gold-ion-attached resin particle dispersion (42.4 ml) was added to 1580 ml of pure water, a 528 mM dimethylamine borane aqueous solution (10 ml) was added dropwise for 2 minutes with stirring at 160 rpm and 20° C., and then the mixture was stirred at room temperature for 2 hours, and thus resin-gold composites with an average particle size of 399 nm were obtained. An operation in which the resin-gold composites were precipitated by centrifugation (at 3100 rpm for 60 minutes), a supernatant was removed, and dispersion was then performed again in pure water was performed three times, and purification was then performed according to a dialysis treatment. The concentration was adjusted and thus a 1 wt % resin-gold composite dispersion was obtained. The absorbance of the produced resin-gold composite was measured according to the above method. The result was 0.96. In addition, the average particle size of the formed gold particles was 25.0 nm, and the gold supported amount was 53.2 wt %. In the resin-gold composite, the gold particles included enclose gold particles that were completely enclosed in the resin particle, partially exposed gold particles having a portion that was embedded in the resin particle and a portion that was exposed to the outside of the resin particle, and surface-attached gold particles that were attached to the surface of the resin particle. At least some of the gold particles were distributed three-dimensionally on the surface layer section of the resin particle. Here, 100% of the gold particles were in the surface layer section.

Using the obtained resin-gold composite, the dispersibility when the antibody was bound was evaluated according to the following "dispersibility evaluation." As a result, both the binding buffer solutions a and b were A, but the binding buffer solution c was C. Therefore, in the following evaluation by immunochromatography, binding of influenza antibodies and blocking using bovine serum albumin were performed at a pH of 3.0 (binding buffer solution a).

<Evaluation by Immunochromatography>

A resin-gold composite-labeled antibody dispersion was produced by performing the same operation as in Comparative Example 3.

Using the produced resin-gold composite-labeled antibody dispersion, measurement was performed according to the following immunochromatography, and the performance of the resin-gold composite dispersion was evaluated. The results are shown below.

10.00 g) were dissolved in 300 g of pure water, 2-vinylpyridine (2-VP, 49.50 g) and divinylbenzene (DVB, 0.50 g) were then added thereto, and stirred at 150 rpm and 30° C. for 50 minutes and then at 60° C. for 30 minutes under a nitrogen atmosphere. After the stirring, 2,2-azobis(2-methylpropionamidine)dihydrochloride (AIBA, 0.250 g) dissolved in 18.00 g of pure water was added dropwise for 2 minutes, and stirred at 150 rpm and 60° C. for 3.5 hours, and thus resin particles with an average particle size of 370 nm were obtained. An operation in which precipitation was performed by centrifugation (at 9000 rpm for 60 minutes), a supernatant was removed, and dispersion was then performed again in pure water was performed three times, and impurities were then removed by a dialysis treatment. Then, the concentration was adjusted and a 10 wt % resin particle dispersion was obtained.

1233 ml of pure water was added to the resin particle dispersion (50 ml), and a 30 mM chloroauric acid aqueous solution (100 ml) was then added thereto, and the mixture was left at room temperature for 24 hours. Then, an operation in which resin particles were precipitated by centrifugation (at 3100 rpm for 30 minutes) and a supernatant was removed was performed three times, and thus an excess chloroauric acid was removed. Then, the concentration was adjusted and a 2.5 wt % gold-ion-attached resin particle dispersion was prepared.

Next, the 2.5 wt % gold-ion-attached resin particle dispersion (42.4 ml) was added to 1580 ml of pure water, a 528 mM dimethylamine borane aqueous solution (10 ml) was added dropwise for 2 minutes with stirring at 160 rpm and 20° C., and then the mixture was stirred at room temperature for 2 hours, and thus resin-gold composites with an average particle size of 393 nm were obtained. An operation in which the resin-gold composites were precipitated by centrifugation (at 3100 rpm for 60 minutes), a supernatant was removed, and dispersion was then performed again in pure water was performed three times, and purification was then performed according to a dialysis treatment. Then the concentration was adjusted and a 1 wt % resin-gold composite dispersion was obtained. The absorbance of the produced resin-gold composite was measured according to the above method. The result was 0.92. In addition, the average

TABLE 15

| | | Slot No. | | | | | | | | | | | |
|---|---|---|---|---|---|---|---|---|---|---|---|---|---|
| | | 1 | 2 | 3 | 4 | 5 | 6 | 7 | 8 | 9 | 10 | 11 | 12 |
| Antigen dilution series | | APC × 1 | APC × 2 | APC × 4 | APC × 8 | APC × 16 | APC × 32 | APC × 64 | APC × 128 | APC × 256 | APC × 512 | APC × 1024 | Negative control |
| Color development level | After 5 minutes | 4.5 | 4.0 | 3.5 | 3.0 | 2.5 | 1.5 | 1.0 | 0.5 | 0.1 | 0 | 0 | 0 |
| | After 10 minutes | 5.5 | 5.0 | 4.5 | 4.0 | 3.5 | 2.5 | 1.5 | 0.5 | 0.5 | 0.1 | 0 | 0 |
| | After 15 minutes | 6.5 | 5.5 | 5.0 | 4.5 | 4.0 | 3.0 | 1.5 | 1.0 | 0.5 | 0.1 | 0 | 0 |

Based on the Table 15, it was confirmed that the resin-gold composite-labeled antibody exhibited favorable color development with respect to antigens diluted 256-fold.

Comparative Example 5

<Synthesis of Resin Particles>

ALIQUAT® 336 [made by Aldrich Co.] (3.00 g) and polyethylene glycol methyl ether methacrylate (PEGMA, particle size of the formed gold particles was 14.9 nm, and the gold supported amount was 55.8 wt %. In the resin-gold composite, the gold particles included enclose gold particles that were completely enclosed in the resin particle, partially exposed gold particles having a portion that was embedded in the resin particle and a portion that was exposed to the outside of the resin particle, and surface-attached gold particles that were attached to the surface of the resin particle. At least some of the gold particles were distributed three-dimensionally on the surface layer section of the resin particle. Here, 71% of the gold particles were in the surface layer section.

Using the obtained resin-gold composite, the dispersibility when the antibody was bound was evaluated according to the following "dispersibility evaluation." As a result, both the binding buffer solutions a and b were A, but the binding buffer solution c was C. Therefore, in the following evaluation by immunochromatography, binding of influenza antibodies and blocking using bovine serum albumin were performed at a pH of 3.0 (binding buffer solution a).

<Evaluation by Immunochromatography>

A resin-gold composite-labeled antibody dispersion was produced by performing the same operation as in Comparative Example 3.

Using the produced resin-gold composite-labeled antibody dispersion, measurement was performed according to the following immunochromatography, and the performance of the resin-gold composite dispersion was evaluated. The results are shown below.

excess chloroauric acid was removed. Then, the concentration was adjusted and a 2.5 wt % gold-ion-attached resin particle dispersion was prepared.

Next, the 2.5 wt % gold-ion-attached resin particle dispersion (42.4 ml) was added to 1580 ml of pure water, a solution in which a 528 mM dimethylamine borane aqueous solution (10 ml) and a 528 mM boric acid aqueous solution (10 ml) were mixed was added dropwise for 4 minutes with stirring at 160 rpm and 20° C., and then the mixture was stirred at room temperature for 2 hours, and thus resin-gold composites with an average particle size of 295 nm were obtained. An operation in which the resin-gold composites were precipitated by centrifugation (at 3100 rpm for 60 minutes), a supernatant was removed, and dispersion was then performed again in pure water was performed three times, and purification was then performed according to a dialysis treatment. Then the concentration was adjusted and a 1 wt % resin-gold composite dispersion was obtained. The absorbance of the produced resin-gold composite was measured according to the above method. The result was 1.35.

TABLE 16

| | | Slot No. | | | | | | | | | | | |
|---|---|---|---|---|---|---|---|---|---|---|---|---|---|
| | | 1 | 2 | 3 | 4 | 5 | 6 | 7 | 8 | 9 | 10 | 11 | 12 |
| Antigen dilution series | | APC × 1 | APC × 2 | APC × 4 | APC × 8 | APC × 16 | APC × 32 | APC × 64 | APC × 128 | APC × 256 | APC × 512 | APC × 1024 | Negative control |
| Color development level | After 5 minutes | 4.0 | 3.0 | 1.0 | 0.5 | 0.1 | 0 | 0 | 0 | 0 | 0 | 0 | 0 |
| | After 10 minutes | 4.5 | 3.5 | 2.0 | 1.5 | 1.0 | 0.5 | 0.1 | 0 | 0 | 0 | 0 | 0 |
| | After 15 minutes | 5.0 | 4.0 | 3.0 | 2.5 | 2.0 | 1.0 | 0.5 | 0.1 | 0 | 0 | 0 | 0 |

Based on the above Table 16, it was confirmed that the resin-gold composite-labeled antibody exhibited favorable color development with respect to antigens diluted 64-fold.

Comparative Example 6

<Synthesis of Resin Particles>

2-vinylpyridine (2-VP, 9.945 g) and divinylbenzene (DVB, 0.097 g) were added to 450 g of pure water, and stirred at 150 rpm and 30° C. for 50 minutes and then at 60° C. for 30 minutes under a nitrogen atmosphere. After the stirring, 2,2-azobis(2-methylpropionamidine)dihydrochloride (AIBA, 0.100 g) dissolved in 10.00 g of pure water was added dropwise for 2 minutes and stirred at 150 rpm and 60° C. for 3.5 hours, and thus resin particles with an average particle size of 290 nm were obtained. An operation in which precipitation was performed by centrifugation (at 9000 rpm for 60 minutes), a supernatant was removed, and dispersion was then performed again in pure water was performed three times, and impurities were then removed by a dialysis treatment. Then, the concentration was adjusted and a 10 wt % resin particle dispersion was obtained.

1233 ml of pure water was added to the above resin particle dispersion (50 ml), and a 30 mM chloroauric acid aqueous solution (100 ml) was then added thereto, and the mixture was left at room temperature for 24 hours. Then, an operation in which resin particles were precipitated by centrifugation (at 3100 rpm for 30 minutes) and a supernatant was removed was performed three times, and thus an In addition, the average particle size of the formed gold particles was 9.0 nm, and the gold supported amount was 50.4 wt %. In the resin-gold composite, the gold particles included enclose gold particles that were completely enclosed in the resin particle, partially exposed gold particles having a portion that was embedded in the resin particle and a portion that was exposed to the outside of the resin particle, and surface-attached gold particles that were attached to the surface of the resin particle. At least some of the gold particles were distributed three-dimensionally on the surface layer section of the resin particle.

Using the obtained resin-gold composite, the dispersibility when the antibody was bound was evaluated according to the following "dispersibility evaluation." As a result, both the binding buffer solutions a and b were A, but the binding buffer solution c was C. Therefore, in the following evaluation by immunochromatography, binding of influenza antibodies and blocking using bovine serum albumin were performed at a pH of 3.0 (binding buffer solution a).

<Evaluation by Immunochromatography>

A resin-gold composite-labeled antibody dispersion was produced by performing the same operation as in Comparative Example 3.

Using the produced resin-gold composite-labeled antibody dispersion, measurement was performed according to the following immunochromatography, and the performance of the resin-gold composite dispersion was evaluated. The results are shown below.

TABLE 17

| Antigen dilution series | | Slot No. | | | | | | | | | | | |
|---|---|---|---|---|---|---|---|---|---|---|---|---|---|
| | | 1 | 2 | 3 | 4 | 5 | 6 | 7 | 8 | 9 | 10 | 11 | 12 |
| | | APC × 1 | APC × 2 | APC × 4 | APC × 8 | APC × 16 | APC × 32 | APC × 64 | APC × 128 | APC × 256 | APC × 512 | APC × 1024 | Negative control |
| Color development level | After 5 minutes | 4.5 | 3.5 | 2.5 | 2.0 | 1.5 | 0.5 | 0.1 | 0 | 0 | 0 | 0 | 0 |
| | After 10 minutes | 5.0 | 4.0 | 3.5 | 2.5 | 2.0 | 1.0 | 0.5 | 0.1 | 0 | 0 | 0 | 0 |
| | After 15 minutes | 5.5 | 4.5 | 4.0 | 2.5 | 2.0 | 1.0 | 0.5 | 0.1 | 0.1 | 0 | 0 | 0 |

Based on the Table 17, it was confirmed that the resin-gold composite-labeled antibody exhibited favorable color development with respect to antigens diluted 64-fold.

Comparative Example 7

<Synthesis of Resin Particles>
2-vinylpyridine (2-VP, 9.90 g) and divinylbenzene (DVB, 0.10 g) were added to 450 g of pure water, and stirred at 150 rpm and 30° C. for 50 minutes and then at 60° C. for 30 minutes under a nitrogen atmosphere. After the stirring, 2,2-azobis(2-methylpropionamidine)dihydrochloride (AIBA, 0.100 g) dissolved in 10.00 g of pure water was added dropwise for 2 minutes, and stirred at 150 rpm and 60° C. for 3.5 hours, and thus resin particles with an average particle size of 110 nm were obtained. An operation in which precipitation was performed by centrifugation (at 9000 rpm for 120 minutes), a supernatant was removed, and dispersion was then performed again in pure water was performed three times, and impurities were then removed by a dialysis treatment. Then, the concentration was adjusted and a 10 wt % resin particle dispersion was obtained.

1233 ml of pure water was added to the above resin particle dispersion (50 ml), and a 30 mM chloroauric acid aqueous solution (100 ml) was then added thereto, and the mixture was left at room temperature for 24 hours. Then, an operation in which resin particles were precipitated by centrifugation (at 3100 rpm for 30 minutes) and a supernatant was removed was performed three times, and thus an excess chloroauric acid was removed. Then, the concentration was adjusted and a 2.5 wt % gold-ion-attached resin particle dispersion was prepared.

Next, the 2.5 wt % gold-ion-attached resin particle dispersion (42.4 ml) was added to 1580 ml of pure water, a solution in which a 528 mM dimethylamine borane aqueous solution (10 ml) and a 528 mM boric acid aqueous solution (10 ml) were mixed was added dropwise for 4 minutes with stirring at 160 rpm and 20° C., and then the mixture was stirred at room temperature for 2 hours, and thus resin-gold composites with an average particle size of 120 nm were obtained. An operation in which the resin-gold composites were precipitated by centrifugation (at 3100 rpm for 60 minutes), a supernatant was removed, and dispersion was then performed again in pure water was performed three times, and purification was then performed according to a dialysis treatment. Then the concentration was adjusted and a 1 wt % resin-gold composite dispersion was obtained. The absorbance of the produced resin-gold composite was measured according to the above method. The result was 1.14. In addition, the average particle size of the formed gold particles was 13.0 nm, and the gold supported amount was 52.0 wt %. In the resin-gold composite, the gold particles included enclose gold particles that were completely enclosed in the resin particle, partially exposed gold particles having a portion that was embedded in the resin particle and a portion that was exposed to the outside of the resin particle, and surface-attached gold particles that were attached to the surface of the resin particle. At least some of the gold particles were distributed three-dimensionally on the surface layer section of the resin particle.

Using the obtained resin-gold composite, the dispersibility when the antibody was bound was evaluated according to the following "dispersibility evaluation." As a result, both the binding buffer solutions a and b were A, but the binding buffer solution c was C. Therefore, in the following evaluation by immunochromatography, binding of influenza antibodies and blocking using bovine serum albumin were performed at a pH of 3.0 (binding buffer solution a).

<Evaluation by Immunochromatography>
A resin-gold composite-labeled antibody dispersion was produced by performing the same operation as in Comparative Example 3.

Using the produced resin-gold composite-labeled antibody dispersion, measurement was performed according to the following immunochromatography, and the performance of the resin-gold composite dispersion was evaluated. The results are shown below.

TABLE 18

| Antigen dilution series | | Slot No. | | | | | | | | | | | |
|---|---|---|---|---|---|---|---|---|---|---|---|---|---|
| | | 1 | 2 | 3 | 4 | 5 | 6 | 7 | 8 | 9 | 10 | 11 | 12 |
| | | APC × 1 | APC × 2 | APC × 4 | APC × 8 | APC × 16 | APC × 32 | APC × 64 | APC × 128 | APC × 256 | APC × 512 | APC × 1024 | Negative control |
| Color development level | After 5 minutes | 5.0 | 4.0 | 3.0 | 2.0 | 1.0 | 0.5 | 0 | 0 | 0 | 0 | 0 | 0 |
| | After 10 minutes | 6.0 | 5.0 | 4.0 | 2.5 | 1.5 | 0.5 | 0 | 0 | 0 | 0 | 0 | 0 |
| | After 15 minutes | 7.0 | 6.0 | 4.5 | 3.0 | 2.0 | 0.5 | 0 | 0 | 0 | 0 | 0 | 0 |

Based on the above Table 18, it was confirmed that the resin-gold composite-labeled antibody exhibited favorable color development with respect to antigens diluted 32-fold.

The measurement results of the absorbance at 570 nm in the above Comparative Examples 1 to 7 are summarized in Table 19.

TABLE 19

|  | Comparative Example 1 | Comparative Example 2 | Comparative Example 3 | Comparative Example 4 | Comparative Example 5 | Comparative Example 6 | Comparative Example 7 |
|---|---|---|---|---|---|---|---|
| Absorbance at 570 nm | 0.83 | 1.32 | 0.98 | 0.96 | 0.92 | 1.35 | 1.14 |
| Evaluation | B | A | A | A | A | A | A |

Example 10

ALIQUAT® 336 [made by Aldrich Co.] (1.00 g) and polyethylene glycol methyl ether methacrylate (PEGMA, 10.00 g) were dissolved in 300 g of pure water, 4-vinylpyridine (4-VP, 48.00 g) and divinylbenzene (DVB, 2.00 g) were then added thereto, and stirred at 150 rpm and 30° C. for 50 minutes and then at 60° C. for 30 minutes under a nitrogen atmosphere. After the stirring, 2,2-azobis(2-methylpropionamidine)dihydrochloride (AIBA, 0.500 g) dissolved in 18.00 g of pure water was added dropwise for 2 minutes and stirred at 150 rpm and 60° C. for 3.5 hours, and thus resin particles with an average particle size of 438 nm were obtained. An operation in which precipitation was performed by centrifugation (at 9000 rpm for 45 minutes), a supernatant was removed and dispersion was then performed again in water was performed three times, and impurities were then removed by a dialysis treatment. Then, the concentration was adjusted and a 10 wt % resin particle dispersion was obtained.

245 ml of pure water was added to the resin particle dispersion (90 ml), a 400 mM chloroplatinic acid aqueous solution (90 ml) was then added thereto and the mixture was stirred at 60 rpm and 30° C. for 3 hours and then left at room temperature for 24 hours. Then, an operation in which the resin particles were precipitated by centrifugation (at 3100 rpm for 30 minutes) and a supernatant was removed was performed three times, and thus an excess chloroplatinic acid was removed. Then, the concentration was adjusted and a dispersion with 5 wt % platinum ions-attached resin particles was prepared.

Next, the dispersion with 5 wt % platinum ions-attached resin particles (55 ml) was added to 3825 ml of pure water and a 132 mM dimethylamine borane aqueous solution (110 ml) was added dropwise for 20 minutes with stirring at 160 rpm and 3° C., and then stirred at 160 rpm and 3° C. for 1 hour. Then, the mixture was stirred at 160 rpm and 25° C. for 3 hours, and thus resin-platinum composites with an average particle size of 447 nm were obtained. An operation in which the resin-platinum composites were precipitated by centrifugation (at 3100 rpm for 60 minutes), a supernatant was removed, and dispersion was then performed again in pure water was performed three times, and impurities were then removed by purification according to a dialysis treatment. Then, the concentration was adjusted and a 1 wt % resin-platinum composite dispersion was obtained. The absorbance of the produced resin-platinum composite was measured according to the above method. The result was 0.80. In addition, the average particle size of the formed platinum particles was 5 nm, and the supported amount of platinum was 37.5 wt %. In the resin-platinum composite, the platinum particles included enclosed platinum particles that were completely enclosed in the resin particle, partially exposed platinum particles having a portion that was embedded in the resin particle and a portion that was exposed to the outside of the resin particle, and surface-attached platinum particles that were attached to the surface of the resin particle. At least some of the platinum particles were distributed three-dimensionally on the surface layer section of the resin particle.

Example 11

ALIQUAT® 336 [made by Aldrich Co.] (1.00 g) and polyethylene glycol methyl ether methacrylate (PEGMA, 10.00 g) were dissolved in 300 g of pure water, 3-vinylpyridine (3-VP, 48.00 g) and divinylbenzene (DVB, 2.00 g) were then added thereto, and stirred at 150 rpm and 30° C. for 50 minutes and then at 60° C. for 30 minutes under a nitrogen atmosphere. After the stirring, 2,2-azobis(2-methylpropionamidine)dihydrochloride (AIBA, 0.500 g) dissolved in 18.00 g of pure water was added dropwise for 2 minutes and stirred at 150 rpm and 60° C. for 3.5 hours, and thus resin particles with an average particle size of 429 nm were obtained. An operation in which precipitation was performed by centrifugation (at 9000 rpm for 45 minutes), a supernatant was removed, and dispersion was then performed again in pure water was performed three times, and impurities were then removed by a dialysis treatment. Then, the concentration was adjusted and a 10 wt % resin particle dispersion was obtained.

245 ml of pure water was added to the resin particle dispersion (90 ml), a 400 mM chloroplatinic acid aqueous solution (90 ml) was then added thereto and the mixture was stirred at 60 rpm and 30° C. for 3 hours and then left at room temperature for 24 hours. Then, an operation in which the resin particles were precipitated by centrifugation (at 3100 rpm for 30 minutes) and a supernatant was removed was performed three times, and thus an excess chloroplatinic acid was removed. Then, the concentration was adjusted and a dispersion with 5 wt % platinum ions-attached resin particles was prepared.

Next, the dispersion with 5 wt % platinum ions-attached resin particles (55 ml) was added to 3825 ml of pure water and a 132 mM dimethylamine borane aqueous solution (110 ml) was added dropwise for 20 minutes with stirring at 160 rpm and 3° C., and then stirred at 160 rpm and 3° C. for 1 hour. Then, the mixture was stirred at 160 rpm and 25° C. for 3 hours and thus resin-platinum composites with an average particle size of 436 nm were obtained. An operation in which the resin-platinum composites were precipitated by centrifugation (at 3100 rpm for 60 minutes), a supernatant was removed, and dispersion was then performed again in pure water was performed three times, and impurities were then removed by purification according to a dialysis treatment. Then, the concentration was adjusted and a 1 wt % resin-platinum composite dispersion was obtained. The absorbance of the produced resin-platinum composite was measured according to the above method. The result was 0.81. In addition, the average particle size of the formed platinum particles was 5 nm, and the supported amount of platinum was 38.1 wt %. In the resin-platinum composite, the platinum particles included enclosed platinum particles that were completely enclosed in the resin particle, partially exposed platinum particles having a portion that was embedded in the resin particle and a portion that was exposed to the outside of the resin particle, and surface-attached platinum particles that were attached to the surface of the resin particle. At least some of the platinum particles were distributed three-dimensionally on the surface layer section of the resin particle.

Example 12

2-(diisopropylamino)ethylmethacrylate (DPA, 10.3 g), poly(propylene glycol)diacrylate (0.2 g) and polyethylene glycol methyl ether methacrylate (PEGMA, 2.0 g) were dissolved in 85 g of pure water, and then stirred at 150 rpm and 30° C. for 50 minutes and then at 70° C. for 30 minutes under a nitrogen atmosphere. After the stirring, ammonium peroxodisulfate (ASP, 0.10 g) dissolved in 2.00 g of pure water was added dropwise for 2 minutes and stirred at 150 rpm and 70° C. for 3.5 hours, and thus resin particles with an average particle size of 338 nm were obtained. An operation in which precipitation was performed by centrifugation (at 9000 rpm for 45 minutes), a supernatant was removed, and dispersion was then performed again in pure water was performed three times, and impurities were then removed by a dialysis treatment. Then, the concentration was adjusted and a 10 wt % resin particle dispersion was obtained.

245 ml of pure water was added to the resin particle dispersion (90 ml), a 400 mM chloroplatinic acid aqueous solution (90 ml) was then added thereto and the mixture was stirred at 60 rpm and 30° C. for 3 hours and then left at room temperature for 24 hours. Then, an operation in which the resin particles were precipitated by centrifugation (at 3100 rpm for 30 minutes) and a supernatant was removed was performed three times, and thus an excess chloroplatinic acid was removed. Then, the concentration was adjusted and a dispersion with 5 wt % platinum ions-attached resin particles was prepared.

Next, the dispersion with 5 wt % platinum ions-attached resin particles (55 ml) was added to 3825 ml of pure water and a 132 mM dimethylamine borane aqueous solution (110 ml) was added dropwise for 20 minutes with stirring at 160 rpm and 3° C., and then stirred at 160 rpm and 3° C. for 1 hour. Then, the mixture was stirred at 160 rpm and 25° C. for 3 hours and thus resin-platinum composites with an average particle size of 351 nm were obtained. An operation in which the resin-platinum composites were precipitated by centrifugation (at 3100 rpm for 60 minutes), a supernatant was removed, and dispersion was then performed again in pure water was performed three times, and impurities were then removed by purification according to a dialysis treatment. Then, the concentration was adjusted and a 1 wt % resin-platinum composite dispersion was obtained. The absorbance of the produced resin-platinum composite was measured according to the above method. The result was 0.75. In addition, the average particle size of the formed platinum particles was 6 nm, and the supported amount of platinum was 37.9 wt %. In the resin-platinum composite, the platinum particles included enclosed platinum particles that were completely enclosed in the resin particle, partially exposed platinum particles having a portion that was embedded in the resin particle and a portion that was exposed to the outside of the resin particle, and surface-attached platinum particles that were attached to the surface of the resin particle. At least some of the platinum particles were distributed three-dimensionally on the surface layer section of the resin particle.

Example 13

A 400 mM chloroplatinic acid aqueous solution (36 ml) was added to the 1 wt % resin-platinum composite dispersion (45 ml) produced in Example 9 and stirred at 60 rpm and 30° C. for 3 hours, and then left at room temperature for 24 hours. Then, an operation in which the resin particles were precipitated by centrifugation (at 2500 rpm for 30 minutes) and a supernatant was removed was performed three times, and thus an excess chloroplatinic acid was removed. Then, the concentration was adjusted and a resin-platinum composite dispersion with 10 wt % of the platinum ions attached thereto was prepared.

Next, the resin-platinum composite dispersion with 10 wt % of the platinum ions attached thereto (5.5 ml) was added to 383 ml of pure water and a 132 mM dimethylamine borane aqueous solution (110 ml) was added dropwise for 120 minutes with stirring at 160 rpm and 3° C., and then stirred at 160 rpm and 3° C. for 1 hour. Then, the mixture was stirred at 160 rpm and 25° C. for 3 hours and thus resin-platinum composites with an average particle size of 454 nm were obtained. An operation in which the resin-platinum composites were precipitated by centrifugation (at 2500 rpm for 60 minutes), a supernatant was removed, and dispersion was then performed again in pure water was performed three times, and impurities were then removed by purification according to a dialysis treatment. Then, the concentration was adjusted and a 1 wt % resin-platinum composite dispersion was obtained. The absorbance of the produced resin-platinum composite was measured according to the above method. The result was 1.02. In addition, the average particle size of the formed platinum particles was 38 nm, and the supported amount of platinum was 51.0 wt %. In the resin-platinum composite, the platinum particles included enclosed platinum particles that were completely enclosed in the resin particle, partially exposed platinum particles having a portion that was embedded in the resin particle and a portion that was exposed to the outside of the resin particle, and surface-attached platinum particles that were attached to the surface of the resin particle. At least some of the platinum particles were distributed three-dimensionally on the surface layer section of the resin particle.

Example 14

ALIQUAT® 336 [made by Aldrich Co.] (0.50 g) and polyethylene glycol methyl ether methacrylate (PEGMA, 10.00 g) were dissolved in 300 g of pure water, 2-vinylpyridine (2-VP, 48.00 g) and divinylbenzene (DVB, 2.00 g) were then added thereto and stirred at 150 rpm and 30° C. for 50 minutes and then at 60° C. for 30 minutes under a nitrogen atmosphere. After the stirring, 2,2-azobis(2-methylpropionamidine)dihydrochloride (AIBA, 0.500 g) dissolved in 18.00 g of pure water was added dropwise for 0.5 minutes and stirred at 150 rpm and 60° C. for 3.5 hours, and thus resin particles with an average particle size of 613 nm were obtained. An operation in which precipitation was performed by centrifugation (at 9000 rpm for 40 minutes), a supernatant was removed, and dispersion was then performed again in pure water was performed three times, impurities were then removed by a dialysis treatment. Then, the concentration was adjusted and a 10 wt % resin particle dispersion was obtained.

245 ml of pure water was added to the resin particle dispersion (90 ml), a 400 mM chloroplatinic acid aqueous solution (90 ml) was then added thereto and the mixture was stirred at 60 rpm and 30° C. for 3 hours and then left at room temperature for 24 hours. Then, an operation in which the resin particles were precipitated by centrifugation (at 3100 rpm for 30 minutes) and a supernatant was removed was performed three times, and thus an excess chloroplatinic acid was removed. Then, the concentration was adjusted and a dispersion with 5 wt % platinum ions-attached resin particles was prepared.

Next, the dispersion with 5 wt % platinum ions-attached resin particles (55 ml) was added to 3825 ml of pure water and a 132 mM dimethylamine borane aqueous solution (110 ml) was added dropwise for 20 minutes with stirring at 160 rpm and 3° C., and then stirred at 160 rpm and 3° C. for 1 hour. Then, the mixture was stirred at 160 rpm and 25° C. for 3 hours and thus resin-platinum composites with an average particle size of 675 nm were obtained. An operation in which the resin-platinum composites were precipitated by centrifugation (at 3100 rpm for 60 minutes), a supernatant was removed, and dispersion was then performed again in pure water was performed three times, and impurities were then removed by purification according to a dialysis treatment. Then, the concentration was adjusted and a 1 wt % resin-platinum composite dispersion was obtained. The absorbance of the produced resin-platinum composite was measured according to the above method. The result was 0.85. In addition, the average particle size of the formed platinum particles was 7 nm, and the supported amount of platinum was 38.2 wt %. In the resin-platinum composite, the platinum particles included enclosed platinum particles that were completely enclosed in the resin particle, partially exposed platinum particles having a portion that was embedded in the resin particle and a portion that was exposed to the outside of the resin particle, and surface-attached platinum particles that were attached to the surface of the resin particle. At least some of the platinum particles were distributed three-dimensionally on the surface layer section of the resin particle.

Example 15

<Synthesis of Resin Particles>

ALIQUAT® 336 [made by Aldrich Co.] (5.00 g) and polyethylene glycol methyl ether methacrylate (PEGMA, 10.00 g) were dissolved in 389.5 g of pure water, 2-vinylpyridine (2-VP, 48.00 g) and divinylbenzene (DVB, 2.00 g) were then added thereto, and stirred at 150 rpm and 30° C. for 50 minutes and then at 60° C. for 30 minutes under a nitrogen atmosphere. After the stirring, 2,2-azobis(2-methylpropionamidine)dihydrochloride (AIBA, 0.500 g) dissolved in 50.00 g of pure water was added dropwise for 2 minutes and stirred at 150 rpm and 60° C. for 3.5 hours, and thus resin particles with an average particle size of 200 nm were obtained. An operation in which precipitation was performed by centrifugation (at 9000 rpm for 60 minutes), a supernatant was removed, and dispersion was then performed again in pure water was performed three times, and impurities were then removed by a dialysis treatment. Then, the concentration was adjusted and a 10 wt % resin particle dispersion was obtained.

308 ml of pure water was added to the resin particle dispersion (80 ml), a 400 mM chloroplatinic acid aqueous solution (12 ml) was then added thereto, and stirred at 60 rpm and 30° C. for 3 hours, and the mixture was then left at room temperature for 24 hours. Then, an operation in which the resin particles were precipitated by centrifugation (at 5100 rpm for 30 minutes) and a supernatant was removed was performed three times, and thus an excess chloroplatinic acid was removed. Then, the concentration was adjusted and a dispersion with 5 wt % platinum ions-attached resin particles was prepared.

Next, the dispersion with 5 wt % platinum ions-attached resin particles (55 ml) was added to 3825 ml of pure water and a 132 mM dimethylamine borane aqueous solution (110 ml) was added dropwise for 20 minutes with stirring at 160 rpm and 3° C., and then stirred at 160 rpm and 3° C. for 1 hour. Then, the mixture was stirred at 160 rpm and 25° C. for 3 hours and thus resin-platinum composites with an average particle size of 205 nm were obtained. An operation in which the resin-platinum composites were precipitated by centrifugation (at 5100 rpm for 60 minutes), a supernatant was removed, and dispersion was performed again in pure water was performed three times, and impurities were then removed by purification according to a dialysis treatment. Then, the concentration was adjusted and a 1 wt % resin-platinum composite dispersion was obtained. The absorbance of the produced resin-platinum composite was measured according to the above method. The result was 0.17. In addition, the average particle size of the formed platinum particles was 5 nm, and the supported amount of platinum was 7.1 wt %. In the resin-platinum composite, the platinum particles included enclosed platinum particles that were completely enclosed in the resin particle, partially exposed platinum particles having a portion that was embedded in the resin particle and a portion that was exposed to the outside of the resin particle, and surface-attached platinum particles that were attached to the surface of the resin particle. At least some of the platinum particles were distributed three-dimensionally on the surface layer section of the resin particle.

Example 16

<Synthesis of Resin Particles>

ALIQUAT® 336 [made by Aldrich Co.] (5.00 g) and polyethylene glycol methyl ether methacrylate (PEGMA, 10.00 g) were dissolved in 389.5 g of pure water, 2-vinylpyridine (2-VP, 48.00 g) and divinylbenzene (DVB, 2.00 g) were then added thereto, and stirred at 150 rpm and 30° C. for 50 minutes and then at 60° C. for 30 minutes under a nitrogen atmosphere. After the stirring, 2,2-azobis(2-methylpropionamidine)dihydrochloride (AIBA, 0.500 g) dissolved in 50.00 g of pure water was added dropwise for 2 minutes and stirred at 150 rpm and 60° C. for 3.5 hours, and thus resin particles with an average particle size of 200 nm were obtained. An operation in which precipitation was performed by centrifugation (at 9000 rpm for 60 minutes), a supernatant was removed, and dispersion was then performed again in pure water was performed three times, and impurities were then removed by a dialysis treatment. Then, the concentration was adjusted and a 10 wt % resin particle dispersion was obtained.

296 ml of pure water was added to the resin particle dispersion (80 ml), a 400 mM chloroplatinic acid aqueous solution (12 ml) was added thereto, and stirred at 60 rpm and 30° C. for 3 hours, and then the mixture was left at room temperature for 24 hours. Then, an operation in which the resin particles were precipitated by centrifugation (at 5100 rpm for 30 minutes) and a supernatant was removed was performed three times, and thus an excess chloroplatinic acid was removed. Then, the concentration was adjusted and a dispersion with 5 wt % platinum ions-attached resin particles was prepared.

Next, the dispersion with 5 wt % platinum ions-attached resin particles (55 ml) was added to 3825 ml of pure water and a 132 mM dimethylamine borane aqueous solution (110 ml) was added dropwise for 20 minutes with stirring at 160 rpm and 3° C., and then stirred at 160 rpm and 3° C. for 1 hour. Then, the mixture was stirred at 160 rpm and 25° C. for 3 hours and thus resin-platinum composites with an average particle size of 210 nm were obtained. An operation in which the resin-platinum composites were precipitated by centrifugation (at 5100 rpm for 60 minutes), a supernatant was removed, and dispersion was then performed again in pure water three times, and impurities were then removed by purification according to a dialysis treatment. Then, the concentration was adjusted and a 1 wt % resin-platinum composite dispersion was obtained. The absorbance of the produced resin-platinum composite was measured according to the above method. The result was 0.33. In addition, the average particle size of the formed platinum particles was 5 nm, and the supported amount of platinum was 15.4 wt %. In the resin-platinum composite, the platinum particles included enclosed platinum particles that were completely enclosed in the resin particle, partially exposed platinum particles having a portion that was embedded in the resin particle and a portion that was exposed to the outside of the resin particle, and surface-attached platinum particles that were attached to the surface of the resin particle. At least some of the platinum particles were distributed three-dimensionally on the surface layer section of the resin particle.

Example 17

A process in which the platinum ions were attached to the resin-platinum composite obtained in Example 3 and a reduction process using a dimethylamine borane aqueous solution were additionally performed once (twice in total), and thus a 1 wt % resin-platinum composite dispersion was obtained. The absorbance of the resin-platinum composite dispersion produced in this manner was measured according to the above method. The result was 1.07. In addition, the average particle size of the formed platinum particles was 9 nm, the supported amount of platinum was 51.0 wt %, and the average particle size of the resin-platinum composites was 399 nm.

In addition, a process in which the platinum ions were attached and a reduction process using a dimethylamine borane aqueous solution were additionally performed twice (four times in total), and thus a resin-platinum composite dispersion was obtained. The absorbance of the 1 wt % resin-platinum composite dispersion produced in this manner was measured according to the above method. The result was 1.24. In addition, the average particle size of the formed platinum particles was 11 nm, the supported amount of platinum was 59.1 wt %, and the average particle size of the resin-platinum composites was 403 nm.

The measurement results of the absorbance at 700 nm in the above Examples 10 to 17 are summarized in Table 20 and Table 21.

TABLE 20

|  | Example 10 | Example 11 | Example 12 | Example 13 | Example 14 |
|---|---|---|---|---|---|
| Absorbance at 700 nm | 0.80 | 0.81 | 0.75 | 1.02 | 0.85 |
| Evaluation | A | A | A | A | A |

TABLE 21

|  | Example 15 | Example 16 | Example 17 | |
|---|---|---|---|---|
| Absorbance at 700 nm | 0.17 | 0.33 | 1.07(*1) | 1.24(*2) |
| Evaluation | B | B | A | A |

(*1)twice the number of reductions
(*2)four times the number of reductions

[Test Examples Regarding Production of Labeled Antibody]

Production Example 1

<Synthesis of Resin Particles>

ALIQUAT® 336 [made by Aldrich Co.] (1.00 g) and polyethylene glycol methyl ether methacrylate (PEGMA, 2.00 g) were dissolved in 80 g of pure water, 2-vinylpyridine (2-VP, 9.90 g) and divinylbenzene (DVB, 0.100 g) were then added thereto and stirred at 250 rpm and 60° C. for 30 minutes under a nitrogen atmosphere. After the stirring, 2,2-azobis(2-methylpropionamidine)dihydrochloride (AIBA, 0.100 g) dissolved in 9.00 g of pure water was added dropwise for 5 minutes and stirred at 250 rpm and 60° C. for 6 hours, and thus resin particles with an average particle size of 0.36 μm were obtained. The resin particles were precipitated by centrifugation (at 9000 rpm for 10 minutes), a supernatant was removed, and dispersion was then performed again in pure water, and a 2.1 wt % resin particle dispersion was obtained.

<Synthesis of Resin-Platinum Composite>

A 30 mM chloroplatinic acid aqueous solution (42.7 g) was added to the 2.1 wt % resin particle dispersion (7.62 g) and the mixture was left at room temperature for 24 hours. Then, the resin particles were precipitated by centrifugation (at 3000 rpm for 10 minutes), a supernatant was removed, and an excess chloroplatinic acid was then removed. Then, dispersion was performed again in 16 g of pure water and a platinum ions-attached resin particle dispersion was prepared. The platinum ions-attached resin particle dispersion (16 g) was added dropwise to a 3.3 mM dimethylamine borane aqueous solution (640 ml) for 2 minutes, and then stirred at 3° C. for 1 hour, and additionally stirred at room temperature for 3 hours, and thus resin-platinum composites with an average particle size of 0.37 μm were obtained. The resin-platinum composites were precipitated by centrifugation (at 3000 rpm for 120 minutes), a supernatant was removed, an appropriate amount of pure water was then added thereto, dispersion was performed again, and purification was performed by an ultrafilter, and thus a 1 wt % resin-platinum composite dispersion was obtained. The absorbance of the resin-platinum composite in the resin-platinum composite dispersion was measured according to the above method. The result was 0.70. In addition, in the resin-platinum composite in the resin-platinum composite dispersion, the average particle size of the platinum particles was 3 nm, and the supported amount of platinum was 33.3 wt %. In the resin-platinum composite, the platinum particles included enclosed platinum particles that were completely enclosed in the resin particle, partially exposed platinum particles having a portion that was embedded in the resin particle and a portion that was exposed to the outside of the resin particle, and surface-attached platinum particles that were attached to the surface of the resin particle. At least some of the platinum particles were distributed three-dimensionally on the surface layer section of the resin particle.

Production Example 2

<Synthesis of Resin-Gold Composite>

A 30 mM chloroauric acid aqueous solution (106.6 g) was added to the 2.1 wt % resin particle dispersion (19.09 g) synthesized in Production Example 1 and the mixture was left at room temperature for 24 hours. Then, the resin particles were precipitated by centrifugation (at 3000 rpm for 10 minutes), a supernatant was removed, an excess chloroauric acid was removed, and dispersions was then performed again in 40 g of pure water, and thus a gold-ion-attached resin particle dispersion was prepared. The gold-ion-attached resin particle dispersion (20 g) was added dropwise to a 3.3 mM dimethylamine borane aqueous solution (600 ml) for 4 minutes, then stirred at 8° C. for 1 hour, and additionally stirred at room temperature for 5 hours, and thus resin-gold composites with an average particle size of 0.38 μm were obtained. The resin-gold composites were precipitated by centrifugation (at 3000 rpm for 120 minutes), a supernatant was removed, an appropriate amount of pure water was then added thereto, dispersion was performed again, and purification was performed by an ultrafilter, and thus a 1 wt % resin-gold composite dispersion was obtained. The absorbance of the resin-gold composite in the resin-gold composite dispersion was measured according to the above method. The result was 1.0. In addition, in the resin-gold composite, the average particle size of the gold particles was 22.0 nm, and the gold supported amount was 49.1 wt %. In the resin-gold composite, the gold particles included enclose gold particles that were completely enclosed in the resin particle, partially exposed gold particles having a portion that was embedded in the resin particle and a portion that was exposed to the outside of the resin particle, and surface-attached gold particles that were attached to the surface of the resin particle. At least some of the gold particles were distributed three-dimensionally on the surface layer section of the resin particle.

Reagent and the Like

The following reagents and the like were used in the test examples and reference test examples.

Anti-influenza type A monoclonal antibody (7.15 mg/mL/PBS): made by Adtec Co.

Binding buffer solution a: 100 mM boric acid solution was adjusted to pH≈8.5 with NaOH.

Binding buffer solution b: 100 mM boric acid solution was adjusted to pH≈7.5 with NaOH.

Blocking buffer solution a: 1 weight % bovine serum albumin solution was adjusted to pH≈8.5 with HCl.

Blocking buffer solution b: 1 weight % bovine serum albumin solution was adjusted to pH≈9.5 with HCl.

Washing buffer solution: 5 mM tris solution was adjusted to pH≈8.5 with HCl.

Storage buffer solution: sucrose was added to a washing buffer solution so that the concentration was 10 weight %.

Influenza type A positive control (APC): influenza type A virus inactivating antigens (made by Adtec Co.) were diluted 100-fold using a specimen treated solution (made by Adtec Co.) and prepared. The antigen concentration of the APC corresponded to 5000 FFU/ml.

Negative control: specimen treated solution (made by Adtec Co.)

PtNCP beads: the resin-platinum composite obtained in Production Example 1 (1 weight %; average particle size of 370 nm)

AuNCP beads: the resin-gold composite obtained in Production Example 2 (1 weight %; average particle size of 380 nm)

Test Example 1

(Binding Process)

0.1 mL of the PtNCP beads as the resin-metal composite were put into a micro tube [IBIS (registered trademark; made by AS ONE Corporation) 2 mL], and 0.9 mL of a binding buffer solution was added thereto. The mixture was sufficiently mixed by turning and mixing, 100 μg of the anti-influenza type A monoclonal antibody was then added thereto, and turned and stirred at room temperature for 3 hours, and a labeled antibody-containing solution A-1 including the anti-influenza type A monoclonal antibody labeled with a resin-platinum composite was obtained.

(Blocking Process)

Next, the labeled antibody-containing solution A-1 was cooled by ice, centrifugation was then performed at 12000 rpm for 5 minutes, a supernatant was removed, 1 mL of the blocking buffer solution a was then added to solid residues, and an ultrasonic dispersion treatment was performed for 10 to 20 seconds, and additionally turning and stirring were performed at room temperature for 2 hours, and a labeled antibody-containing solution B-1 was obtained.

(Washing Treatment)

Next, the labeled antibody-containing solution B-1 was cooled by ice, centrifugation was then performed at 12000 rpm for 5 minutes, a supernatant was removed, 1 mL of the washing buffer solution was then added to solid residues, and an ultrasonic dispersion treatment was performed for 10 to 20 seconds. This operation was performed three times to perform the washing treatment.

(Storage Treatment)

Next, after being cooled by ice, centrifugation was performed at 12000 rpm for 5 minutes, a supernatant was removed, 1 mL of the storage buffer solution was then added to solid residues, and an ultrasonic dispersion treatment was performed 10 to 20 seconds, and thus a labeled antibody-containing solution C-1 was obtained.

<Performance Evaluation>

3 μL of the labeled antibody-containing solution C-1 was put into 12 wells of a 96-well plate, and 100ℓ of two-fold serial dilutions (1-fold to 1024-fold dilution, indicated by APC×1 to APC×1024) of the APC and 100 μL of a negative control were mixed. Next, 50 μL of the result was added to a monochrome screen for influenza type A evaluation, and color development levels were evaluated after 5 minutes, after 10 minutes, and after 15 minutes. The results are shown in Table 22. Here, in Table 22, a larger numerical value indicates a higher color development level (stronger color development).

TABLE 22

| | | APC × 1 | APC × 2 | APC × 4 | APC × 8 | APC × 16 | APC × 32 | APC × 64 | APC × 128 | APC × 256 | APC × 512 | APC × 1024 | Negative control |
|---|---|---|---|---|---|---|---|---|---|---|---|---|---|
| Antigen dilution series | | \multicolumn{12}{c}{Labeled antibody-containing solution C-1} |
| Color development level | After 5 minutes | 6.0 | 5.0 | 4.0 | 3.0 | 2.0 | 1.5 | 1.0 | 0.5 | 0.1 | 0 | 0 | 0 |
| | After 10 minutes | 7.0 | 6.0 | 5.0 | 4.0 | 3.0 | 2.5 | 1.5 | 1.0 | 0.5 | 0 | 0 | 0 |
| | After 15 minutes | 7.0 | 7.0 | 6.0 | 5.0 | 4.0 | 3.0 | 2.0 | 1.5 | 0.5 | 0.1 | 0 | 0 |

Based on Table 22, it was confirmed that the labeled antibody-containing solution C-1 exhibited favorable color development with respect to antigens diluted 256-fold, and had excellent labeling performance.

Reference Test Example 1

In the binding process in Test Example 1, when AuNCP beads were used in place of PtNCP beads and the binding buffer solution b was used in place of the binding buffer solution a, since the resin-gold composites aggregated, it was difficult to obtain a labeled antibody-containing solution.

Reference Test Example 2

In the binding process in Test Example 1, when AuNCP beads were used in place of PtNCP beads, since the resin-gold composites aggregated, it was difficult to obtain a labeled antibody-containing solution.

Reference Test Example 3

When AuNCP beads were used in place of PtNCP beads In the binding process in Test Example 1, and the blocking buffer solution b was used in place of the blocking buffer solution a in the blocking process, since the resin-gold composites aggregated, it was difficult to obtain a labeled antibody-containing solution.

While embodiments of the present invention have been described in detail above for the purpose of illustration, the present invention is not limited to the above embodiment. For example, a case in which the resin-platinum composite of the present invention was applied for immunological measurement has been described in detail in the above embodiment. However, the resin-platinum composite of the present invention can be applied for not only immunological measurement but also other applications. In particular, since the resin-platinum composite of the present invention exhibits excellent dispersibility while it is bound to a ligand such as an antigen or an antibody, it is suitable for use in medical applications and the like.

What is claimed is:

1. A resin-platinum composite comprising:
    a resin particle; and
    a plurality of platinum particles that are relatively smaller than the resin particle,
    wherein the plurality of platinum particles are fixed to the resin particle,
    60 wt % to 100 wt % of the plurality of platinum particles are in a surface layer section of the resin particle,
    at least some of the platinum particles are distributed three-dimensionally in the surface layer section of the resin particle,
    the resin particle is a polymer particle having, in a repeating unit of the polymer, a substituent to which platinum ions are able to be attached, wherein the polymer is selected from the group consisting of polyamine, polyamide, polyimide, polypyrrole, and an acrylic resin having a nitrogen atom in a side chain thereof,
    the platinum particles consist of platinum,
    an average particle size of the platinum particles is in a range of 3 to 30 nm,
    an average particle size of the resin-platinum composite is in a range of 100-600 nm,
    a supported amount of the platinum particles is in a range of 5 wt % to 70 wt % with respect to a weight of the resin-platinum composite, and
    20 wt % or less of the platinum particles are surface-attached particles.

2. The resin-platinum composite according to claim 1, wherein the average particle size of the platinum particles is in a range of 5 to 30 nm.

3. The resin-platinum composite according to claim 1, wherein an average particle size of the platinum particles is in a range of 3 to 15 nm.

4. The resin-platinum composite according to claim 1, wherein the supported amount of the platinum particles is in a range of 15 wt % to 60 wt % with respect to the weight of the resin-platinum composite.

5. A labeling substance comprising the resin-platinum composite according to claim 1.

6. The labeling substance according to claim 5 that is used by attaching an antigen or an antibody to the surface of the resin-platinum composite.

7. An immunological measurement method using the labeling substance according to claim 5.

8. A reagent for immunological measurement comprising the resin-platinum composite according to claim 1.

9. An analyte measurement method of detecting or quantifying an analyte contained in a sample, the analyte measurement method comprising performing the following Processes (I) to (III) using a test strip for lateral flow chromatography that comprises a membrane and a determination section to which a capture ligand that specifically binds to the analyte is fixed in the membrane:
    Process (I): a process of contacting the analyte contained in the sample with a labeled antibody obtained by labeling an antibody that specifically binds to the analyte with the resin-platinum composite according to claim 1;
    Process (II): a process of contacting a composite comprising the analyte and the labeled antibody formed in Process (I) with the capture ligand in the determination section; and
    Process (III): a process of measuring a color development intensity derived from localized surface plasmon resonance and light energy absorption due to electron transition of the resin-platinum composite.

10. An analyte measurement kit for detecting or quantifying an analyte contained in a sample using a test strip for lateral flow chromatography, the analyte measurement kit comprising:
the test strip for lateral flow chromatography that comprises a membrane and a determination section to which a capture ligand that specifically binds to the analyte is fixed in the membrane; and
a detection reagent comprising a labeled antibody obtained by labeling an antibody that specifically binds to the analyte with the resin-platinum composite according to claim 1.

11. A test strip for lateral flow chromatography for detecting or quantifying an analyte contained in a sample, the test strip for lateral flow chromatography comprising:
a membrane;
a determination section to which a capture ligand that specifically binds to the analyte is fixed in a direction in which the sample is developed in the membrane; and
a reaction section that is upstream from the determination section and comprises a labeled antibody obtained by labeling an antibody that specifically binds to the analyte with the resin-platinum composite according to claim 1.

* * * * *